US009991449B2

(12) United States Patent
Cha et al.

(10) Patent No.: US 9,991,449 B2
(45) Date of Patent: Jun. 5, 2018

(54) ANTHRACENE DERIVATIVES FOR ORGANIC LIGHT-EMITTING DIODE AND ORGANIC LIGHT-EMITTING DIODE INCLUDING THE SAME

(71) Applicant: SFC CO., LTD., Cheongju-si (KR)

(72) Inventors: Soon-Wook Cha, Goyang-si (KR); Sang-woo Park, Seoul (KR); Seok-Bae Park, Geumsan-gun (KR); Yoona Shin, Seoul (KR); Hee-Dae Kim, Miryang-si (KR)

(73) Assignee: SFC CO., LTD., Cheongju-si (KR)

( * ) Notice: Subject to any disclaimer, the term of this patent is extended or adjusted under 35 U.S.C. 154(b) by 0 days. days.

(21) Appl. No.: 15/543,192

(22) PCT Filed: Jan. 8, 2016

(86) PCT No.: PCT/KR2016/000168
§ 371 (c)(1),
(2) Date: Jul. 12, 2017

(87) PCT Pub. No.: WO2016/117861
PCT Pub. Date: Jul. 28, 2016

(65) Prior Publication Data
US 2018/0006244 A1 Jan. 4, 2018

(30) Foreign Application Priority Data

Jan. 21, 2015 (KR) .................. 10-2015-0009794

(51) Int. Cl.
*C07D 307/93* (2006.01)
*C07D 307/94* (2006.01)
(Continued)

(52) U.S. Cl.
CPC ........ *H01L 51/0073* (2013.01); *C07D 307/93* (2013.01); *C07D 307/94* (2013.01); *C07D 333/78* (2013.01); *C07D 493/10* (2013.01); *C07D 495/10* (2013.01); *C09K 11/025* (2013.01); *H01L 51/0052* (2013.01); *H01L 51/0058* (2013.01); *H01L 51/0074* (2013.01); *H01L 51/5012* (2013.01);
(Continued)

(58) Field of Classification Search
CPC .. C07D 307/93; C07D 307/94; C07D 333/78; C07D 493/10; C07D 495/10; H01L 51/0052; H01L 51/0058; H01L 51/0073; H01L 51/0074; H01L 51/5012
See application file for complete search history.

(56) References Cited

U.S. PATENT DOCUMENTS

2007/0152565 A1* 7/2007 Kubota ................ C07C 15/28
313/504

FOREIGN PATENT DOCUMENTS

KR   1020060113954 A   11/2006
KR     101092006 A   12/2011

OTHER PUBLICATIONS

International Search Report of PCT/KR2016/000168, dated Apr. 19, 2016, English Translation.

* cited by examiner

*Primary Examiner* — Daniel Shook
(74) *Attorney, Agent, or Firm* — STIP Law Group, LLC

(57) ABSTRACT

The present invention relates to a novel anthracene derivative, for an organic light-emitting device, and an organic light-emitting device comprising same, the anthracene derivative enabling excellent device characteristics when used as a light-emitting material.

14 Claims, 1 Drawing Sheet

(51) Int. Cl.
*C07D 333/78* (2006.01)
*C07D 493/10* (2006.01)
*C07D 495/10* (2006.01)
*H01L 51/54* (2006.01)
*C09K 11/06* (2006.01)
*H01L 51/00* (2006.01)
*C09K 11/02* (2006.01)
*H01L 51/50* (2006.01)

(52) U.S. Cl.
CPC ...... *H01L 51/5056* (2013.01); *H01L 51/5072* (2013.01); *H01L 51/5088* (2013.01); *H01L 51/5092* (2013.01)

```
┌─────────────────────────────┐
│           80                │
│───────────────────────────── │
│           70                │
│───────────────────────────── │
│           60                │
│───────────────────────────── │
│           50                │
│───────────────────────────── │
│           40                │
│───────────────────────────── │
│           30                │
│───────────────────────────── │
│           20                │
│───────────────────────────── │
│           10                │
└─────────────────────────────┘
```

ANTHRACENE DERIVATIVES FOR ORGANIC LIGHT-EMITTING DIODE AND ORGANIC LIGHT-EMITTING DIODE INCLUDING THE SAME

CROSS-REFERENCE TO RELATED APPLICATIONS

This application is the U.S. National Phase under 35 U.S.C. § 371 of International Application No. PCT/KR2016/000168 filed on Jan. 8, 2016, which in turn claims the benefit of Korean Application No. 10-2015-0009794, filed on Jan. 21, 2015, the disclosures of which are incorporated by reference into the present application.

TECHNICAL FIELD

The present invention relates to a novel anthracene derivative and an organic light-emitting diode comprising the same and, more particularly, to a novel anthracene derivative for organic light-emitting diodes that exhibits excellent diode characteristics when used as a luminescent material, and an organic light-emitting diode comprising the same.

BACKGROUND ART

Organic light-emitting diodes (OLEDs), based on self-luminescence, enjoy the advantage of having a wide viewing angle and being able to be made thinner and lighter than liquid crystal displays (LCDs). In addition, an OLED display exhibits a very fast response time. Accordingly, OLEDs find applications in the illumination field as well as the full-color display field.

In general, the term "organic light-emitting phenomenon" refers to a phenomenon in which electrical energy is converted to light energy by means of an organic material. An OLED using the organic light-emitting phenomenon has a structure usually comprising an anode, a cathode, and an organic material layer interposed therebetween. In this regard, the organic material layer may be, for the most part, of a multilayer structure consisting of different materials, for example, a hole injecting layer, a hole transport layer, a light-emitting layer, an electron transport layer, and an electron injecting layer, in order to improve the efficiency and stability of the organic light-emitting diode (OLED). In the organic light-emitting diode having such a structure, when a voltage is applied between the two electrodes, a hole injected from the anode migrates to the organic layer while an electron is released from the cathode and moves toward the organic layer. In the luminescent zone, the hole and the electron recombine to produce an exciton. When the exciton returns to the ground state from the excited state, the molecule of the organic layer emits light. Such an organic light-emitting diode is known to have characteristics such as self-luminescence, high luminance, high efficiency, low driving voltage, a wide viewing angle, high contrast, and high-speed response.

Materials used as organic layers in OLEDs may be divided into luminescent materials and charge transport materials, for example, a hole injection material, a hole transport material, an electron injection material, and an electron transport material. As for the luminescent materials, there are two main families of OLED: those based on small molecules and those employing polymers. The light-emitting mechanism forms the basis for classification of the luminescent materials as fluorescent or phosphorescent materials, which use excitons in singlet and triplet states, respectively. Further, luminescent materials may be divided according to color into blue, green, and red light-emitting materials. Furthermore, yellow and reddish yellow light-emitting materials have been developed in order to achieve more natural colors.

Meanwhile, when a single material is employed as the luminescent material, intermolecular actions cause the wavelength of maximum luminescence to shift toward a longer wavelength, decreasing color purity or attenuating light with consequent reduction in the efficiency of the diode. In this regard, a host-dopant system may be used as a luminescent material so as to increase the color purity and the light emission efficiency through energy transfer.

This is based on the principle whereby, when a dopant is smaller in energy band gap than a host accounting for the light-emitting layer, the addition of a small amount of the dopant to the host generates excitons from the light-emitting layer so that the excitons are transported to the dopant, emitting light at high efficiency. Here, light of desired wavelengths can be obtained depending on the kind of dopant because the wavelength of the host moves to the wavelength range of the dopant.

With regard to related arts pertaining to host compounds in the light-emitting layer, reference may be made to Korean Patent No. 10-1092006 (Dec. 9, 2011), which discloses an OLED comprising a luminescent medium layer containing a compound in which an anthracene structure has substituted phenyl groups attached respectively to opposite ends thereof, and Korean Patent Publication No. 10-2006-0113954 A (Nov. 3, 2006), which describes on OLED comprising a luminescent medium layer containing an asymmetric anthracene derivative of a certain structure.

Despite a variety of kinds of compounds prepared for use in luminescent media layers including the related art, there is still the continued need to develop organic layer materials that are stable and of high efficiency.

RELATED ART DOCUMENTS

Korean Patent No. 10-1092006 (Dec. 9, 2011)
Korean Patent Publication No. 10-2006-0113954 A (Nov. 3, 2006)

DETAILED DESCRIPTION OF THE INVENTION

Technical Problem

Accordingly, a purpose of the present disclosure is to provide a novel compound for use in organic light-emitting layers which guarantees outstanding diode properties.

Another purpose of the present disclosure is to provide an OLED comprising the compound.

Technical Solution

In order to accomplish one purpose thereof, the present disclosure provides an organic luminescent compound represented by the following Chemical Formula A:

[Chemical Formula A]

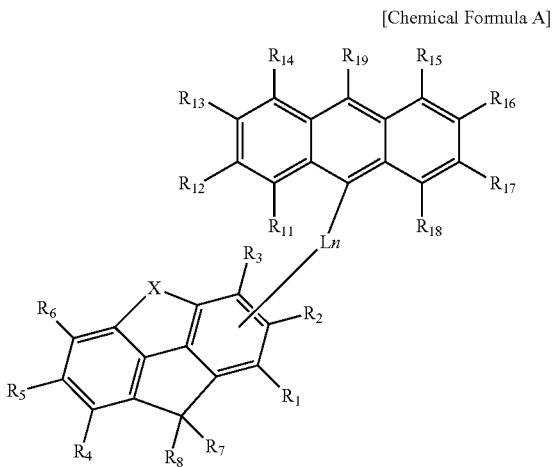

wherein,
X is O or S,
one of R1 to R3 is a single bond connected to linker L;
R1 to R8, and R11 to R19 may be the same or different, and are each independently selected from among a hydrogen atom, a deuterium atom, a substituted or unsubstituted alkyl of 1 to 40 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms bearing at least one selected from among O, N, S, and Si as a heteroatom, a substituted or unsubstituted alkoxy of 1 to 30 carbon atoms, a substituted or unsubstituted aryloxy of 6 to 30 carbon atoms, a substituted or unsubstituted alkylthio of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, a substituted or unsubstituted arylsilyl of 6 to 30 carbon atoms, a cyano, a nitro, and a halogen, with the proviso that R1 to R8, and R11 to R19 may each be connected to an adjacent radical thereof to form an aliphatic or aromatic mono- or polycyclic ring which may bear at least one selected from N, S, and O as a heteroatom;

linker L is a single bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, or a substituted or unsubstituted heteroarylene of 2 to 60 carbon atoms; and n is an integer of 1 to 3, with the proviso that when n is 2 or greater, corresponding L's may be the same or different.

The other purpose of the present disclosure may be accomplished by providing an OLED comprising a first electrode; a second electrode facing the first electrode; and an organic layer interposed therebetween, wherein the organic layer contains at least one of the organic luminescent compounds of the present disclosure.

Advantageous Effects

According to the present disclosure, the organic luminescent compound represented by Chemical Formula A is available in OLEDs and allows for the fabrication of OLEDs which are stable and exhibit high efficiency.

BRIEF DESCRIPTION OF THE DRAWINGS

FIG. 1 is a schematic diagram of an OLED according to some embodiments of the present disclosure.

MODE FOR CARRYING OUT THE INVENTION

Below, a detailed description is given of the present disclosure.

The present disclosure addresses an organic compound for use in a light-emitting layer of OLEDs, represented by the following Chemical Formula A:

[Chemical Formula A]

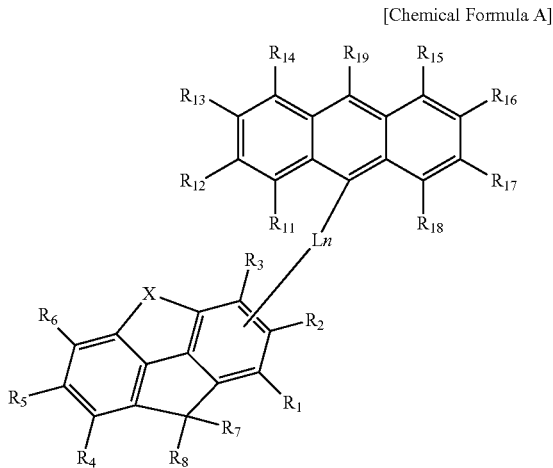

wherein,
X is O or S,
one of R1 to R3 is a single bond connected to linker L;
R1 to R8, and R11 to R19 may be the same or different, and are each independently selected from among a hydrogen atom, a deuterium atom, a substituted or unsubstituted alkyl of 1 to 40 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms bearing at least one selected from among O, N, S, and Si as a heteroatom, a substituted or unsubstituted alkoxy of 1 to 30 carbon atoms, a substituted or unsubstituted aryloxy of 6 to 30 carbon atoms, a substituted or unsubstituted alkylthio of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, a substituted or unsubstituted arylsilyl of 6 to 30 carbon atoms, a cyano, a nitro, and a halogen, with the proviso that R1 to R8, and R11 to R19 may each be connected to an adjacent radical thereof to form an aliphatic or aromatic mono- or polycyclic ring which may bear at least one selected from N, S, and O as a heteroatom;

linker L is a single bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, or a substituted or unsubstituted heteroarylene of 2 to 60 carbon atoms; and n is an integer of 1 to 3, with the proviso that when n is 2 or greater, corresponding L's may be the same or different, wherein the term 'substituted' in the expression 'substituted or unsubstituted' used in Chemical Formula A means having at least one substituent selected from the group consisting of a deuterium, a cyano, a halogen, a hydroxy, a nitro, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, a heteroarylamino of 1 to 24 carbon atoms, an alkylsilyl of 1 to 24 carbon atoms, an arylsilyl of 6 to 24 carbon atoms, and an aryloxy of 6 to 24 carbon atoms.

Count is taken of the range of the alkyl or aryl moiety in phrases "a substituted or unsubstituted alkyl of 1 to 24 carbon atoms", "a substituted or unsubstituted aryl of 6 to 24 carbon atoms", etc., as used herein. The expression for a number of carbon atoms in "a substituted or unsubstituted alkyl of 1 to 24 carbon atoms", "a substituted or unsubstituted aryl of 6 to 24 carbon atoms" means the total number of carbon atoms in the alkyl or aryl radical or moiety alone, exclusive of the number of carbon atoms of the substituent. For instance, a phenyl group with a butyl at the para position falls within the scope of an aryl of 6 carbon atoms, even if it is substituted with a butyl radical of 4 carbon atoms.

As used herein, the term "aryl" as a substituent used in the compounds of the present disclosure refers to an aromatic system consisting of hydrocarbons including one or more rings, and may form an additional ring fused with adjacent substituents attached thereto, if present.

Concrete examples of the aryl include phenyl, o-biphenyl, m-biphenyl, p-biphenyl, o-terphenyl, m-terphenyl, p-terphenyl, naphthyl, anthryl, phenanthryl, pyrenyl, indenyl, fluorenyl, tetrahydronaphthyl, perylenyl, chrysenyl, naphthacenyl, and fluoranthenyl, at least one hydrogen atom of which may be substituted by a deuterium atom, a halogen atom, a hydroxy, a nitro, a cyano, a silyl, an amino (—NH2, —NH(R), or —N(R')(R") wherein R' and R" are each independently an alkyl of 1 to 10 carbon atoms, in this case, called "alkylamino"), an amidino, a hydrazine, a hydrazone, a carboxyl, a sulfonic acid, a phosphoric acid, an alkyl of 1 to 24 carbon atoms, a halogenated alkyl of 1 to 24 carbon atoms, an alkenyl of 1 to 24 carbon atoms, an alkynyl of 1 to 24 carbon atoms, a heteroalkyl of 1 to 24 carbon atoms, an aryl of 6 to 24 carbon atoms, an arylalkyl of 6 to 24 carbon atoms, a heteroaryl of 2 to 24 carbon atoms, or a heteroarylalkyl of 2 to 24 carbon atoms.

The substituent heteroaryl used in the compound of the present disclosure refers to a cyclic aromatic system of 2 to 24 carbon atoms bearing one to three heteroatoms selected from among N, O, P, and S. In the aromatic system, two or more rings may be fused. One or more hydrogen atoms on the heteroaryl may be substituted with the same substituents as in the aryl.

Examples of the substituent alkyl useful in the present disclosure include methyl, ethyl, propyl, isopropyl, isobutyl, sec-butyl, tert-butyl, pentyl, iso-amyl, and hexyl. At least one hydrogen atom of the alkyl may be substituted with the same substituent as in the aryl.

Examples of the substituent alkoxy useful in the present disclosure include methoxy, ethoxy, propoxy, isobutyloxy, sec-butyloxy, pentyloxy, iso-amyloxy, and hexyloxy. At least one hydrogen atom of the alkoxy may be substituted with the same substituent as in the aryl.

Representative among examples of the substituent silyl useful in the present disclosure are trimethylsilyl, triethylsilyl, triphenylsilyl, trimethoxysilyl, dimethoxyphenylsilyl, diphenylmethylsilyl, silyl, diphenylvinylsilyl, methylcyclobutylsilyl, and dimethylfurylsilyl. One or more hydrogen atoms of the silyl may be substituted with the same substituent as in the aryl.

In one embodiment of the present invention, the linker L in the organic luminescent compound represented by Chemical Formula A may be a single bond or one selected from among compounds represented by the following Structural Formulas 1 to 9, and n is 1 or 2:

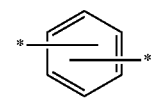

[Structural Formula 1]

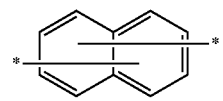

[Structural Formula 2]

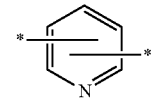

[Structural Formula 3]

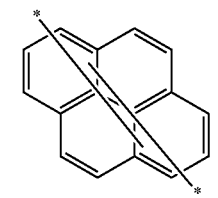

[Structural Formula 4]

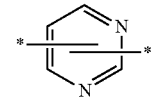

[Structural Formula 5]

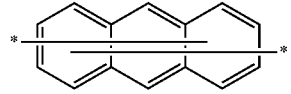

[Structural Formula 6]

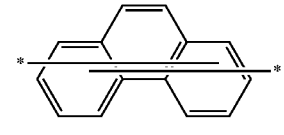

[Structural Formula 7]

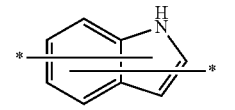

[Structural Formula 8]

[Structural Formula 9]

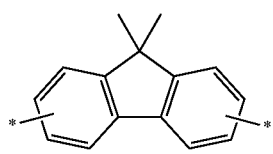

According a particular embodiment of the present disclosure, L may be a single bond or a compound represented by Structural Formula 1 or 2, and n may be 1.

In Structural Formulas 1 to 9, each of the unsubstituted carbon atoms of the aromatic ring moiety is bound with a hydrogen atom or a deuterium atom.

According to another embodiment of the present disclosure, the substituents R7 and R8 in Chemical Formula A may bond to each other to form a ring.

According to another embodiment of the present disclosure, adjacent two of the substituents R4 to R8 may bond to each other to form a ring. In this regard, the substituent R7 or R8 may form a ring with the substituent R4. Further, when adjacent two of the substituents R4 to R6 form a ring moiety, the ring moiety may form an additional ring with one of the remaining substituents R4 to R8 which do not participate in forming the ring moiety.

According to one embodiment of the present disclosure, the substituent R19 in Chemical Formula A may be a substituted or unsubstituted aryl of 6 to 24 carbon atoms.

According to another embodiment, the substituent R19 in Chemical Formula A may be a substituted or unsubstituted aryl of 6 to 24 carbon atoms bearing a deuterium atom on the aromatic ring thereof.

According to another embodiment, the R7 and R8 may each be a substituted or unsubstituted aryl of 6 to 24 carbon atoms.

Representative of the organic luminescent compounds represented by Chemical Formula A of the present disclosure is any one selected from among, but not limited to, compounds represented by the following Chemical Formulas 1 to 24.

<Chemical Formula 1>

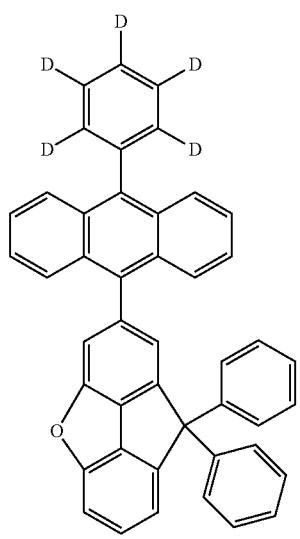

<Chemical Formula 2>

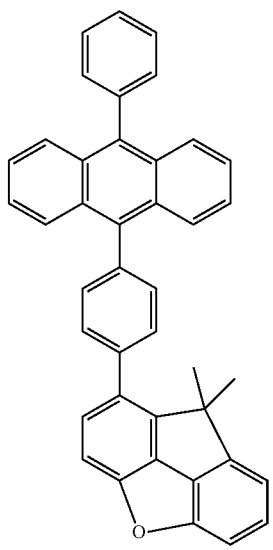

<Chemical Formula 3>

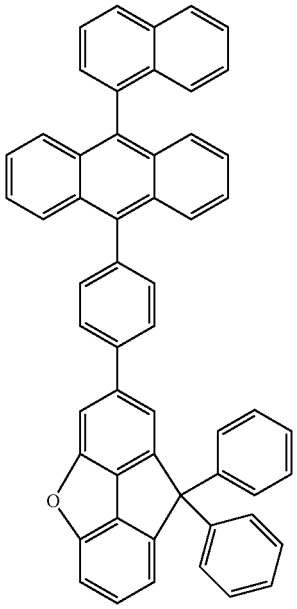

<Chemical Formula 4>
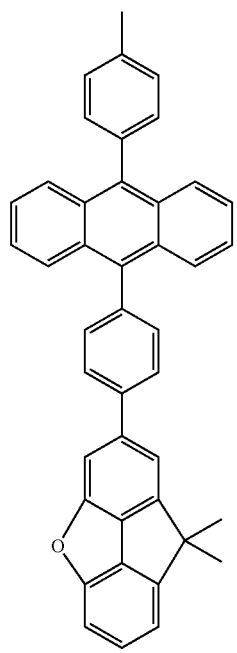
<Chemical Formula 5>
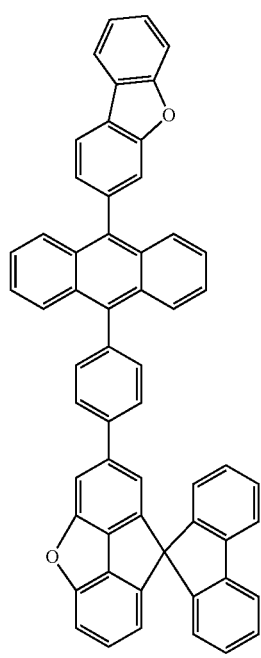
<Chemical Formula 6>
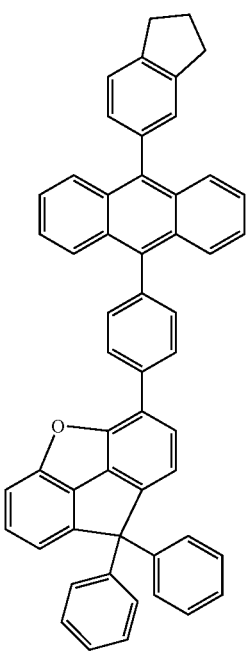
<Chemical Formula 7>
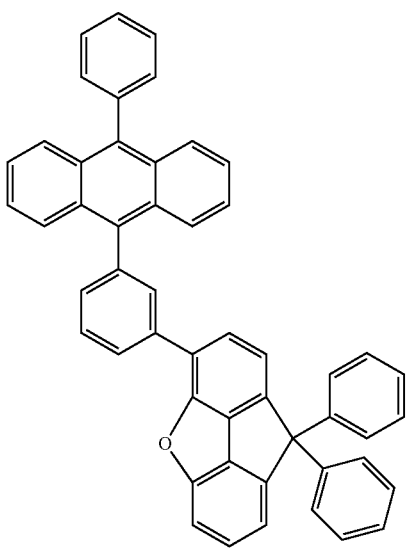

<Chemical Formula 8>
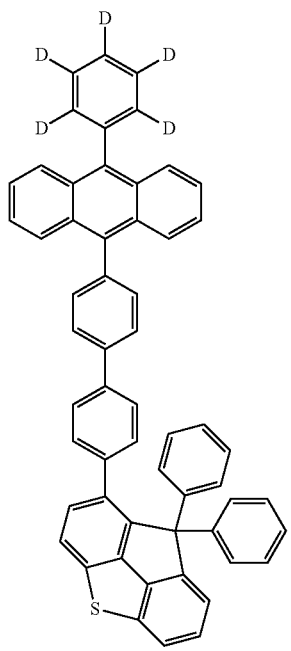
<Chemical Formula 9>
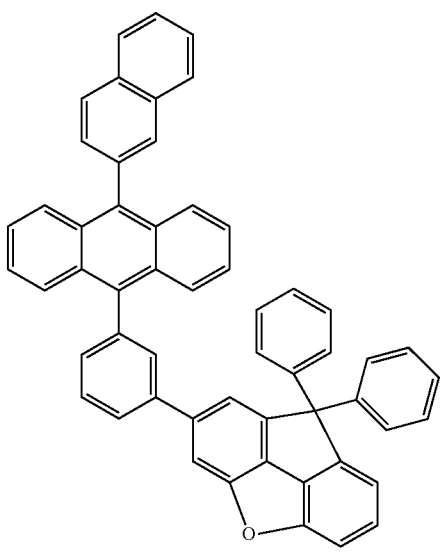
<Chemical Formula 10>
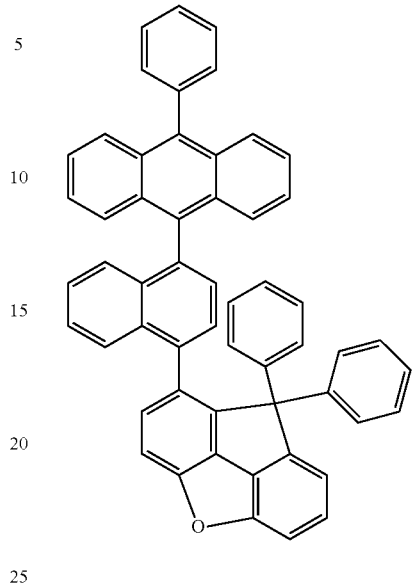
<Chemical Formula 11>
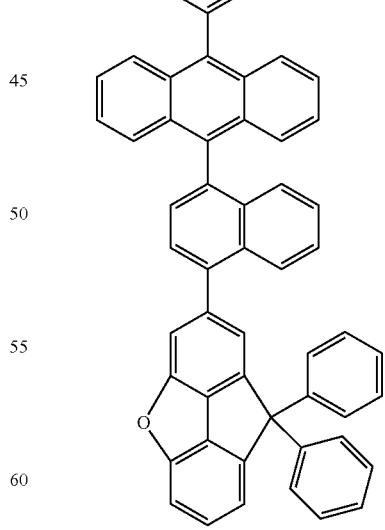

<Chemical Formula 12>
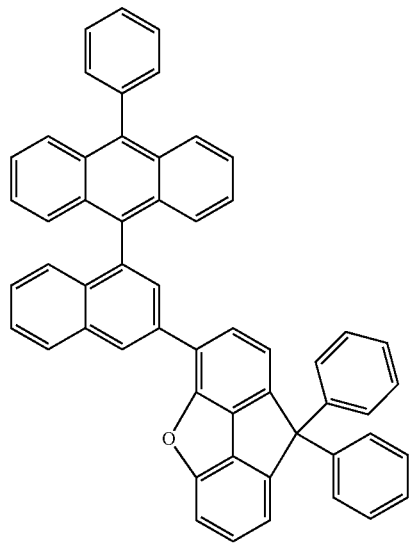
<Chemical Formula 13>
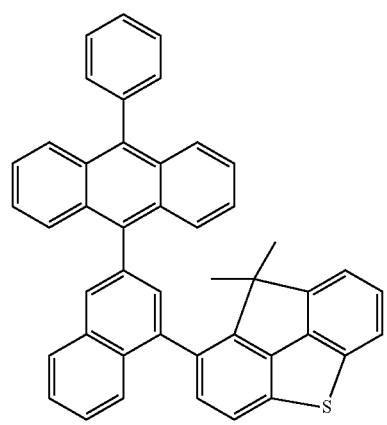
<Chemical Formula 14>
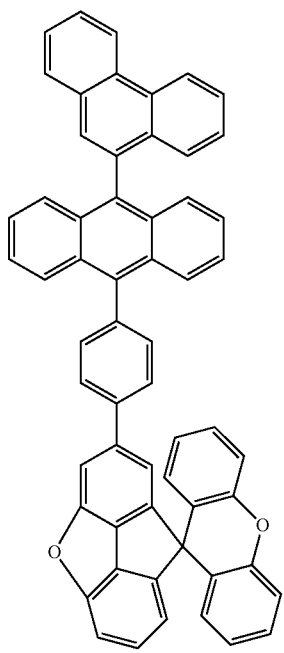
<Chemical Formula 15>
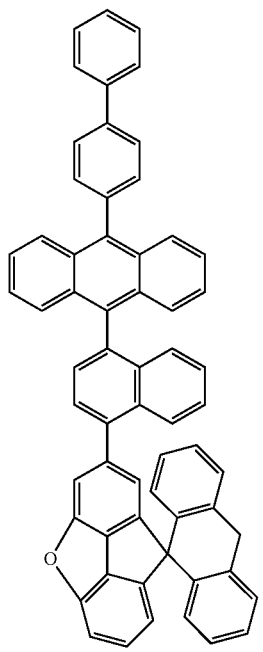
<Chemical Formula 16>

<Chemical Formula 17>
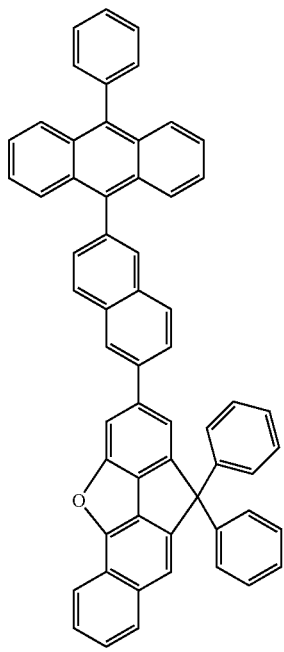
<Chemical Formula 18>
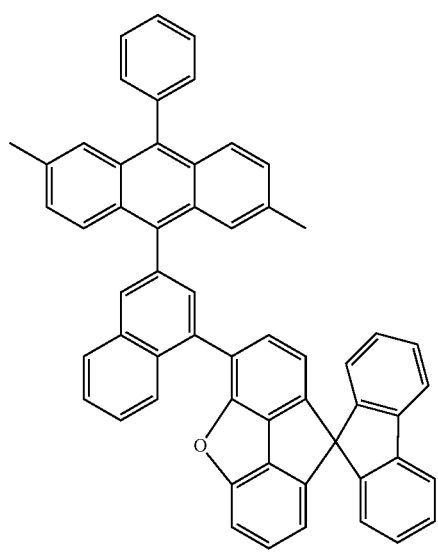
<Chemical Formula 19>
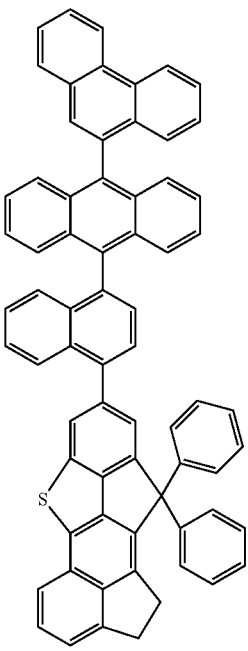
<Chemical Formula 20>
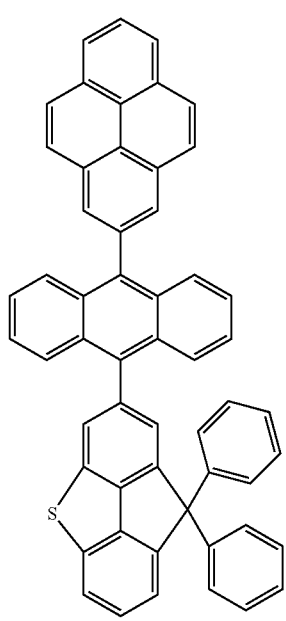

<Chemical Formula 21>

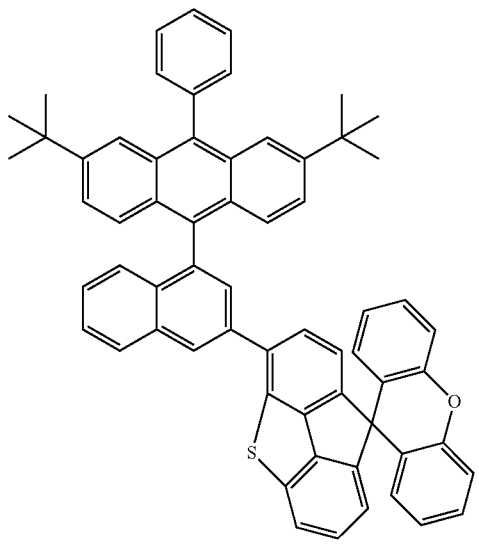

<Chemical Formula 22>

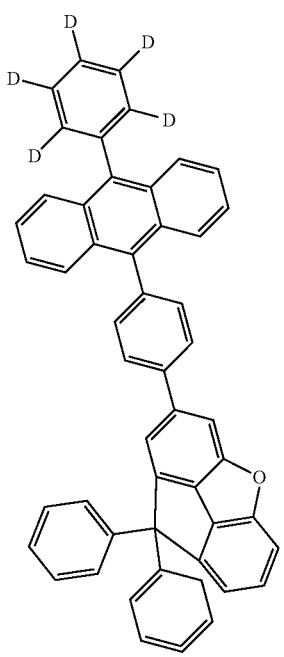

<Chemical Formula 23>

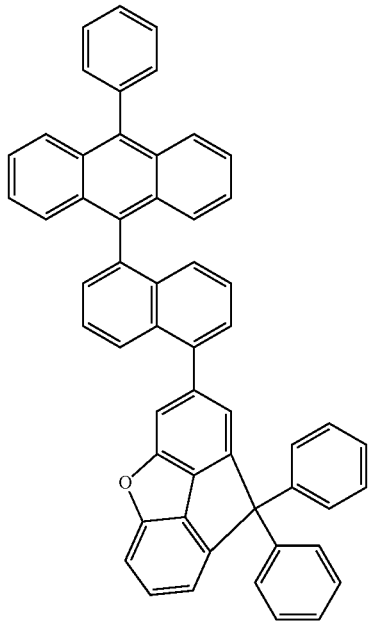

<Chemical Formula 24>

Also, the present disclosure provides an OLED, comprising a first electrode; a second electrode facing the first electrode; and an organic layer interposed therebetween, wherein the organic layer contains at least one of the anthracene derivatives of the present disclosure.

As used herein, the expression "(the organic layer) contains at least one organic compound" is construed to mean that (the organic layer) may contain one organic compound falling within the scope of the present disclosure or two or more different compounds falling within the scope of the present disclosure.

According to some particular embodiments of the present disclosure, the organic layer containing the compound of the present disclosure may comprise at least one of a hole injecting layer, a hole transport layer, a functional layer capable of both hole injection and hole transport, a light-emitting layer, an electron transport layer, and an electron injecting layer.

In addition, the organic layer interposed between the first electrode and the second electrode may be a light-emitting layer. In this regard, the light-emitting layer may be composed of a host and a dopant.

Further, the compound of Chemical Formula A may be used as the host

Concrete examples of the dopant material used in the light-emitting layer include pyrene compounds, deuterium-deuterium-substituted pyrene compounds, aryl amines, deuterium-substituted aryl amines, perylene compounds, deuterium-substituted perylene compounds, pyrrole compounds, deuterium-substituted pyrrole compounds, hydrazone compounds, deuterium-substituted hydrazone compounds, carbazole compounds, deuterium-substituted carbazole compounds, stilbene compounds, deuterium-substituted stilbene compounds, starburst-type compounds, deuterium-substituted starburst-type compounds, oxadiazole compounds, deuterium-substituted oxadiazole compounds, coumarin, and deuterium-substituted coumarin, but are not limited thereto.

When the light-emitting layer comprises a host and a dopant, the content of the dopant in the light-emitting layer may range from about 0.01 to 20 parts by weight based on 100 parts by weight of the host, but is not limited thereto.

Further, one or more layers selected from among a hole injecting layer, a hole transport layer, a functional layer capable of both hole injection and hole transport, a light-emitting layer, an electron transport layer, and an electron injecting layer may be deposited using a single-molecule deposition process or a solution process. Here, the deposition process is a process by which a material is vaporized in a vacuum or at a low pressure and deposited to form a layer, and the solution process is a method in which a material is dissolved in a solvent and applied for the formation of a thin film by means of inkjet printing, roll-to-roll coating, screen printing, spray coating, dip coating, spin coating, etc.

Also, the organic light-emitting diode of the present disclosure may be applied to a device selected from among flat display devices, flexible display devices, monochrome or grayscale flat illumination devices, and monochrome or grayscale flexible illumination devices.

In one embodiment of the present disclosure, a hole transport layer (HTL) may be further deposited between the anode and the organic light-emitting layer while an electron transport layer (ETL) may be further deposited between the cathode and the organic light-emitting layer.

The hole injecting layer that functions to facilitate electron injection from the anode. As a material for the hole transport layer, an electron donating molecule with low ionization potential is used. Predominantly, diamine, triamine or tetraamine derivatives having a triphenylamine skeleton are employed.

So long as it is conventionally used in the art, any hole transport layer material may be available without particular limitations, as exemplified by N,N'-bis(3-methylphenyl)-N,N'-diphenyl-[1,1-biphenyl]-4,4'-diamine (TPD) and N,N'-di(naphthalen-1-yl)-N,N'-diphenylbenzidine (a-NPD).

A hole injecting layer (HIL) may be further deposited beneath the hole transport layer. No particular limitations are imposed on the hole injecting layer material, as long as it is one that is typically used in the art. Examples include CuPc (copperphthalocyanine), and the starburst amines TCTA (4,4',4"-tri(N-carbazolyl)triphenyl-amine), and m-MTDATA (4,4',4"-tris-(3-methylphenylphenyl amino)triphenylamine).

In addition, the electron transport layer used in the OLED according to the present invention functions to smoothly transport electrons supplied from the cathode into the organic luminescent layer and to suppress the migration of holes uncombined in the organic light-emitting layer, thereby increasing the opportunity of recombination between electrons and holes in the light-emitting layer.

Any material that is conventionally used in the art may be employed for the electron transport layer without particular limitations. By way of example, as described above, the oxadiazole derivatives PBD, BMD, and BND, and Alq3 may be used.

An electron injecting layer that functions to facilitate electron injection from the cathode, thus improving the power efficiency of the diode, may be further deposited on the electron transport layer. So long as it is conventionally used in the art, any material can be available for the electron injecting layer without particular limitations. Examples include LiF, NaCl, CsF, Li2O, and BaO.

Below, the organic light-emitting diode of the present disclosure is explained with reference to FIG. 1.

FIG. 1 is a schematic cross-sectional view of the structure of an organic light-emitting diode according to some embodiments of the present disclosure. The organic light-emitting diode comprises an anode 20, a hole transport layer 40, an organic light-emitting layer 50, an electron transport layer 60, and a cathode 80, and optionally a hole injecting layer 30 or an electron injecting layer 70. In addition, one or two intermediate layers may be further formed in the organic light-emitting diode, or a hole barrier layer or an electron barrier layer may also be employed.

Reference is made to FIG. 1 with regard to the organic light-emitting diode of the present disclosure and the fabrication thereof. First, a substrate 10 is coated with an anode electrode material to form an anode 20. So long as it is used in a typical organic EL device, any substrate may be used as the substrate 10. Preferable is an organic substrate or transparent plastic substrate that exhibits excellent transparency, surface smoothness, ease of handling, and waterproofness. As the anode electrode material, indium tin oxide (ITO), indium zinc oxide (IZO), tin oxide (SnO2), or zinc oxide (ZnO), which are transparent and superior in terms of conductivity, may be used.

A hole injecting layer material is applied on the anode electrode 20 by thermal deposition in a vacuum or by spin coating to form a hole injecting layer 30. Subsequently, thermal deposition in a vacuum or by spin coating may also be conducted to form a hole transport layer 40 with a hole transport layer material on the hole injecting layer 30.

Then, an organic light-emitting layer 50 is deposited on the hole transport layer 40, optionally followed by the formation of a hole barrier layer (not shown) on the organic light-emitting layer 50 by deposition in a vacuum or by spin coating. When holes traverse the organic light-emitting layer and are introduced into the cathode, the efficiency and lifespan of the diode are deteriorated. Formed of a material with a low HOMO (Highest Occupied Molecular Orbital) level, the hole barrier layer serves to prevent the introduction of holes into the cathode. Any material that has a higher ionization potential than the light-emitting compound and which is also able to carry electrons may be used for the hole barrier layer without limitation. Representative among hole barrier materials are BAlq, BCP, and TPBI.

Using a vacuum deposition method or a spin-coating method, an electron transport layer 60 may be deposited on the hole barrier layer and may then be overlaid with an electron injection layer 70. A cathode metal is deposited on the electron injection layer 70 by thermal deposition in a vacuum to form a cathode 80, thus obtaining an organic EL diode. Here, the cathode may be made of lithium (Li), magnesium (Mg), aluminum (Al), aluminum-lithium (Al—Li), calcium (Ca), magnesium-indium (Mg—In), or magnesium-silver (Mg—Ag). For a top-emitting OLED, a transparent cathode made of ITO or IZO may be employed.

In some embodiments of the present disclosure, the light-emitting layer particularly ranges in thickness from 50 to 2,000 Å. In addition, the light-emitting layer may be composed of a host and a dopant wherein the host may be the compound of the present disclosure.

The dopant may be a compound represented by Chemical Formula 1 or 2. In this regard, the light-emitting layer may further contain various dopant materials.

[Chemical Formula B]

[Chemical Formula C]

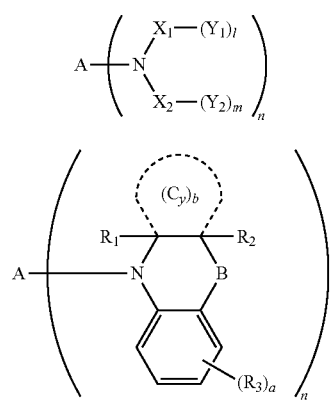

wherein,

A may be any one selected from among a substituted or unsubstituted aryl of 5 to 50 carbon atoms, a substituted or unsubstituted heteroaryl of 3 to 50 carbon atoms bearing O, N, or S as a heteroatom, a substituted or unsubstituted arylene of 6 to 60 carbon atoms, and a substituted or unsubstituted heteroarylene of 3 to 50 carbon atoms bearing O, N, or S as a heteroatom.

In greater detail, A may be a substituted or unsubstituted arylene of 6 to 60 carbon atoms, or a single bond, particularly any one selected from among anthracene, pyrene, phenanthrene, indenophenanthrene, chrysene, naphthacene, pycene, triphenylene, perylene, and pentacene, and more particularly a substituent represented by the following Chemical Formula s A1 to A10:

[Chemical Formula A1]

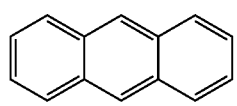

[Chemical Formula A2]

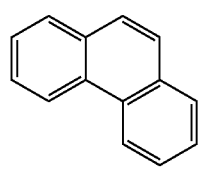

[Chemical Formula A3]

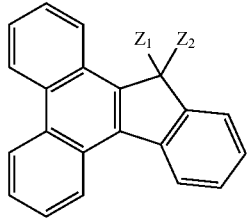

[Chemical Formula A4]

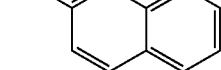

[Chemical Formula A5]

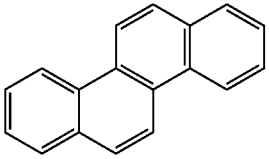

[Chemical Formula A6]

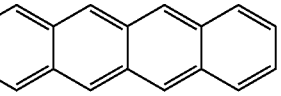

[Chemical Formula A7]

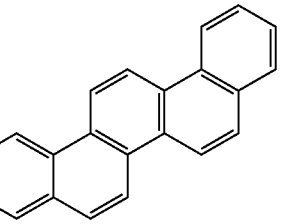

[Chemical Formula A8]

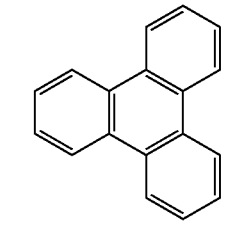

[Chemical Formula A9]

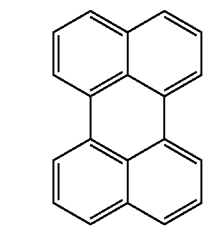

[Chemical Formula A10]

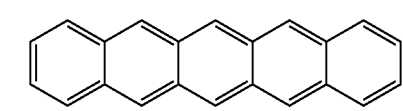

In Chemical Formula A3, Z1 and Z2 may be the same or different and are each independently selected from the group consisting of a hydrogen atom, a deuterium atom, a substituted or unsubstituted alkyl of 1 to 60 carbon atoms, a substituted or unsubstituted alkenyl of 2 to 60 carbon atoms, a substituted or unsubstituted alkynyl of 2 to 60 carbon atoms, a substituted or unsubstituted alkoxy of 1 to 60 carbon atoms, a substituted or unsubstituted alkylthio of 1 to 60 carbon atoms, a substituted or unsubstituted cycloalkyl of 3 to 60 carbon atoms, a substituted or unsubstituted aryl of 6 to 60 carbon atoms, a substituted or unsubstituted aryloxy of 5 to 60 carbon atoms, a substituted or unsubstituted arylthio of 5 to 60 carbon atoms, a substituted or unsubstituted heteroaryl of 2 to 60 carbon atoms, a substituted or unsubstituted (alkyl)amino of 1 to 60 carbon atoms, a di(substituted or unsubstituted alkyl)amino of 1 to 60 carbon atoms or a (substituted or unsubstituted aryl)amino of 6 to 60 carbon atoms, and a di(substituted or unsubstituted aryl) amino of 6 to 60 carbon atoms, with the proviso that Z1 and Z2 may each form a fused ring with an adjacent radical.

In Chemical Formula B,

X1 and X2 may each be independently a substituted or unsubstituted arylene of 6 to 30 carbon atoms or a single bond, with the proviso that X1 and X2 may bond to each other, Y1 and Y2 may be the same or different and are each independently selected from the group consisting of a substituted or unsubstituted aryl of 6 to 24 carbon atoms, a substituted or unsubstituted heteroaryl of 2 to 24 carbon atoms, a substituted or unsubstituted alkyl of 1 to 24 carbon atoms, a substituted or unsubstituted heteroalkyl of 1 to 24 carbon atoms, a substituted or unsubstituted cycloalkyl of 3 to 24 carbon atoms, a substituted or unsubstituted alkoxy of 1 to 24 carbon atoms, a cyano, a halogen, a substituted or unsubstituted aryloxy of 6 to 24 carbon atoms, a substituted or unsubstituted alkylsilyl of 1 to 40 carbon atoms, a substituted or unsubstituted arylsilyl of 6 to 30 carbon atoms, a germanium, a phosphorus, a boron, a deuterium, and a hydrogen, with the proviso that Y1 and Y2 may each form with an aliphatic, aromatic, heteroaliphatic or heteroaromatic fused ring with an adjacent radical, l and m are each an integer of 1 to 20, and n is an integer of 1 to 4.

In Chemical Formula C,

Cy is a substituted or unsubstituted cycloalkyl of 3 to 8 carbon atoms and b is an integer of 1 to 4, with the proviso that when b is 2 or greater, the corresponding cycloalkanes may be the same or different and may be individually in a fused form having a deuterium or an alkyl as a substituent.

In Chemical Formula C,

B is a single bond or —[C(R5)(R6)]p- wherein p is an integer of 1 to 3, with the proviso that when p is 2 or greater, the corresponding R5's and R6's are individually the same or different;

R1, R2, R3, R5, and R6 may each be independently selected from among a hydrogen atom, a deuterium atom, a halogen atom, a hydroxyl, a cyano, a nitro, an amino, an amidino, a hydrazine, a hydrazone, a carboxyl or a salt thereof, a sulfonic acid or a salt thereof, a phosphoric acid or a salt thereof, a substituted or unsubstituted alkyl of 1 to 60 carbon atoms, a substituted or unsubstituted alkenyl of 2 to 60 carbon atoms, a substituted or unsubstituted alkynyl of 2 to 60 carbon atoms, a substituted or unsubstituted alkoxy of 1 to 60 carbon atoms, a substituted or unsubstituted alkylthio of 1 to 60 carbon atoms, a substituted or unsubstituted cycloalkyl of 3 to 60 carbon atoms, a substituted or unsubstituted aryl of 6 to 60 carbon atoms, a substituted or unsubstituted aryloxy of 5 to 60 carbon atoms, a substituted or unsubstituted arylthio of 5 to 60 carbon atoms, a substituted or unsubstituted heteroaryl of 2 to 60 carbon atoms, a substituted or unsubstituted (alkyl)amino of 1 to 60 carbon atoms, a di(substituted or unsubstituted alkyl)amino of 1 to 60 carbon atoms or a (substituted or unsubstituted aryl)amino of 6 to 60 carbon atoms, a di(substituted or unsubstituted aryl)amino of 6 to 60 carbon atoms, a substituted or unsubstituted alkylsilyl of 1 to 40 carbon atoms, a substituted or unsubstituted arylsilyl of 6 to 30 carbon atoms, a germanium, a phosphorus, and a boron, a is an integer of 1 to 4, with the proviso that when a is 2 or greater, the corresponding plural R3's may be the same or different and may be individually in a fused form, and n is an integer of 1 to 4.

The amine radical of Chemical Formula s 1 and 2, which is linked to A, may be represented by any one selected from among, but not limited to, the following Substituents 1 to 52:

The amine radical of Chemical Formulas B and C, which is linked to A, may be represented by any one selected from among, but not limited to, the following Substituents 1 to 52:

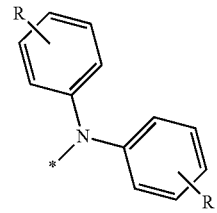

[Substituent 1]

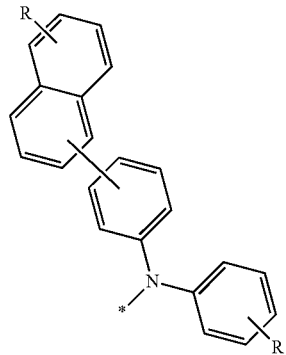

[Substituent 2]

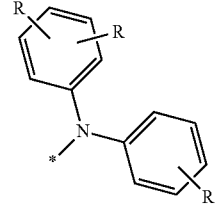

[Substituent 3]

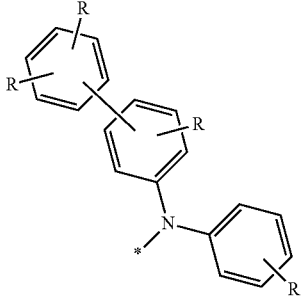

[Substituent 4]

[Substituent 5]
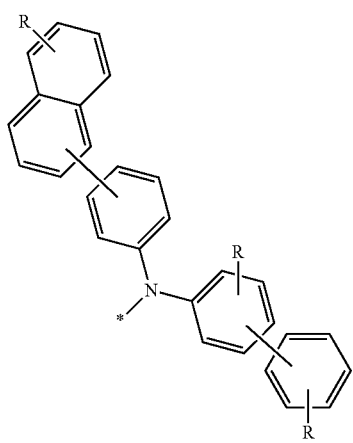
[Substituent 6]
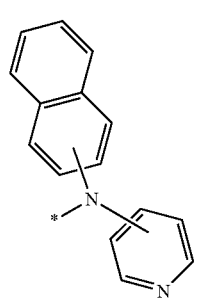
[Substituent 7]
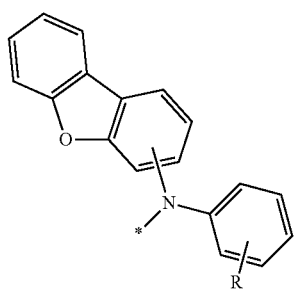
[Substituent 8]
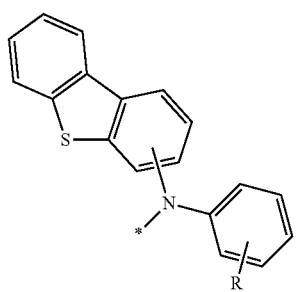
[Substituent 9]
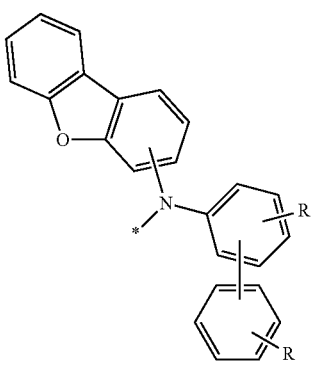
[Substituent 10]
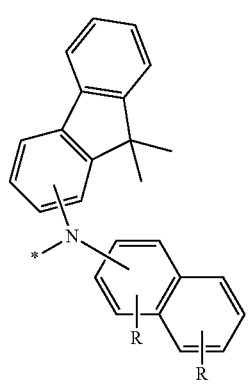
[Substituent 11]
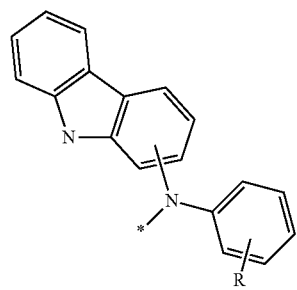
[Substituent 12]
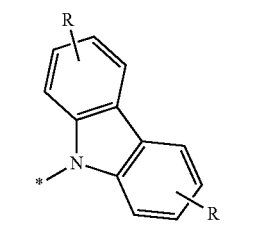
[Substituent 13]
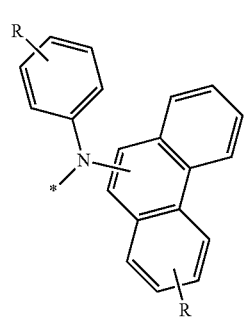

-continued
[Substituent 14]
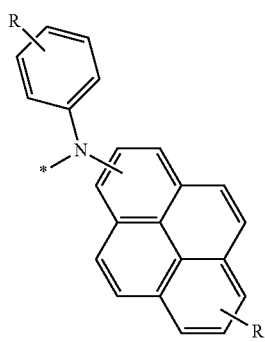
[Substituent 15]
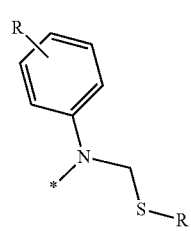
[Substituent 16]
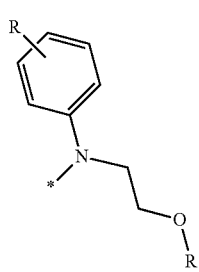
[Substituent 17]
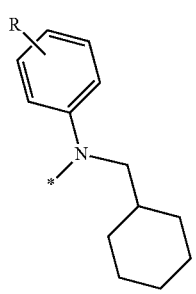
[Substituent 18]
[Substituent 19]
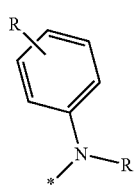
[Substituent 20]
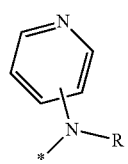
-continued
[Substituent 21]
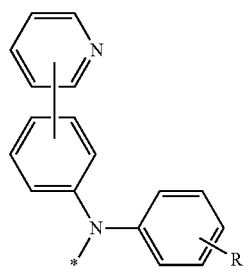
[Substituent 22]
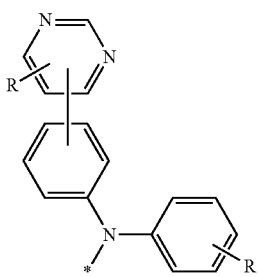
[Substituent 23]
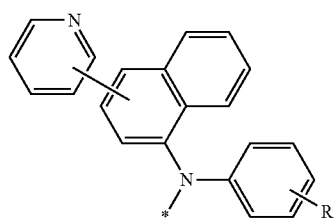
[Substituent 24]
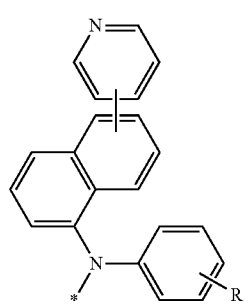
[Substituent 25]
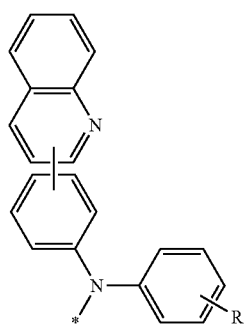

[Substituent 26]
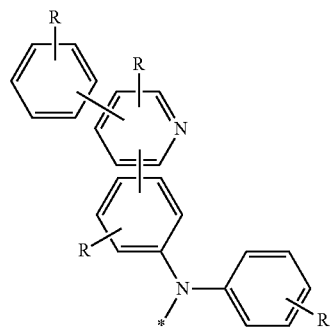
[Substituent 27]
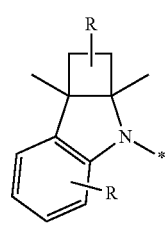
[Substituent 28]
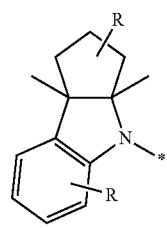
[Substituent 29]
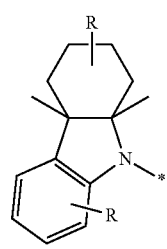
[Substituent 30]
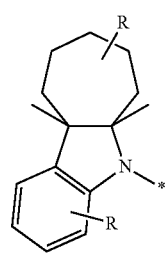
[Substituent 31]
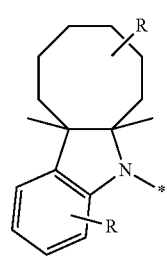
[Substituent 32]
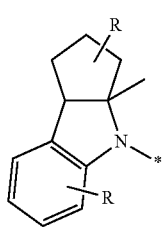
[Substituent 33]
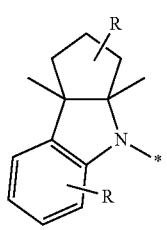
[Substituent 34]
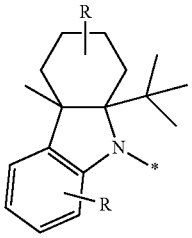
[Substituent 35]
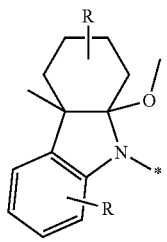
[Substituent 36]
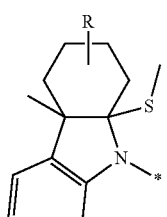
[Substituent 37]
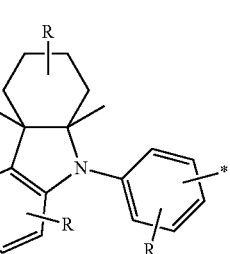

[Substituent 38]
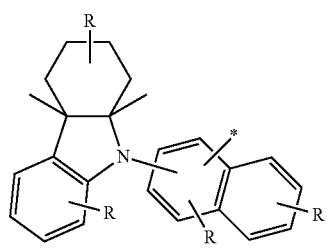
[Substituent 39]
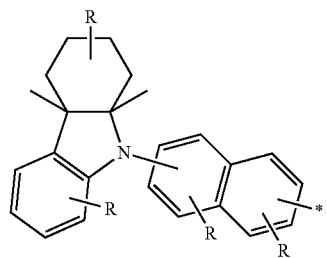
[Substituent 40]
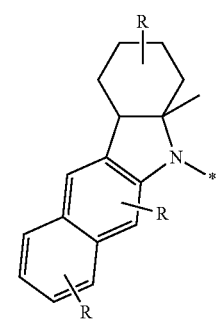
[Substituent 41]
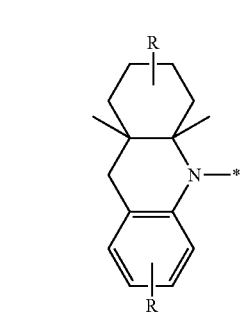
[Substituent 42]
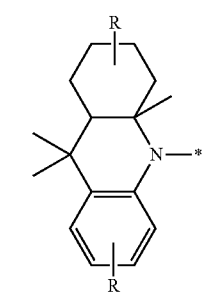
[Substituent 43]
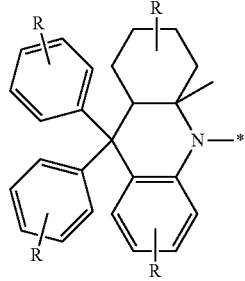
[Substituent 44]
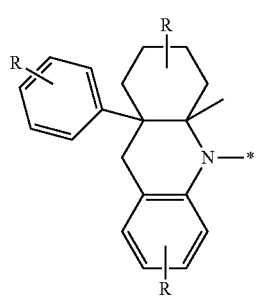
[Substituent 45]
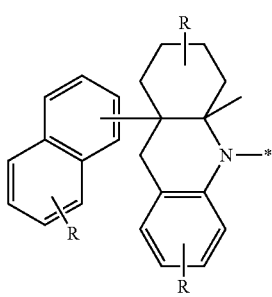
[Substituent 46]
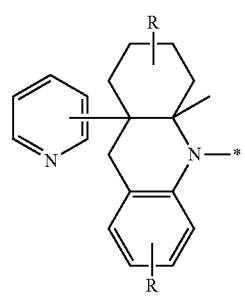
[Substituent 47]
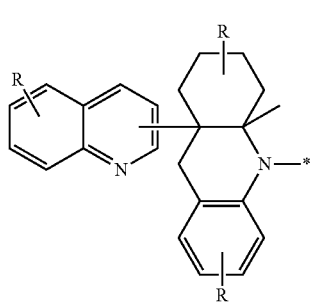

[Substituent 48]

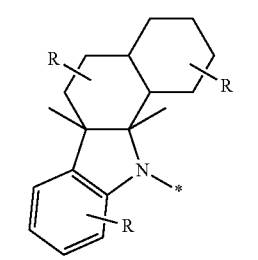

[Substituent 49]

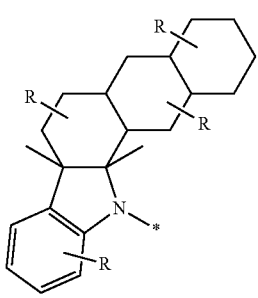

[Substituent 50]

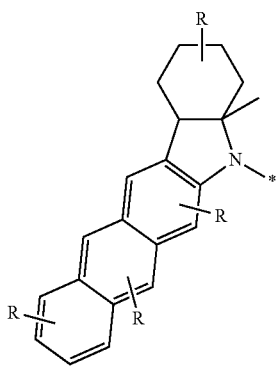

[Substituent 51]

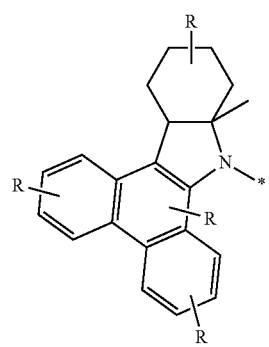

[Substituent 52]

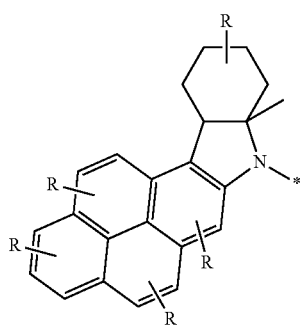

wherein R's may be the same or different and are each independently selected from among a hydrogen atom, a deuterium atom, a halogen atom, a hydroxyl, a cyano, a nitro, an amino, an amidino, a hydrazine, a hydrazone, a carboxyl or a salt thereof, a sulfonic acid or a salt thereof, a phosphoric acid or a salt thereof, a substituted or unsubstituted alkyl of 1 to 60 carbon atoms, a substituted or unsubstituted alkenyl of 2 to 60 carbon atoms, a substituted or unsubstituted alkynyl of 2 to 60 carbon atoms, a substituted or unsubstituted alkoxy of 1 to 60 carbon atoms, a substituted or unsubstituted alkylthio of 1 to 60 carbon atoms, a substituted or unsubstituted cycloalkyl of 3 to 60 carbon atoms, a substituted or unsubstituted aryl of 6 to 60 carbon atoms, a substituted or unsubstituted aryloxy of 5 to 60 carbon atoms, a substituted or unsubstituted arylthio of 5 to 60 carbon atoms, a substituted or unsubstituted heteroaryl of 2 to 60 carbon atoms, a substituted or unsubstituted (alkyl)amino of 1 to 60 carbon atoms, a di(substituted or unsubstituted alkyl)amino of 1 to 60 carbon atoms or a (substituted or unsubstituted aryl)amino of 6 to 60 carbon atoms, a di(substituted or unsubstituted aryl)amino of 6 to 60 carbon atoms, a substituted or unsubstituted alkylsilyl of 1 to 40 carbon atoms, a substituted or unsubstituted arylsilyl of 6 to 30 carbon atoms, a germanium, a phosphorus, and a boron, and may each form a fused ring with an adjacent radical.

A better understanding of the present disclosure may be obtained through the following examples which are set forth to illustrate, but are not to be construed as limiting the present disclosure.

EXAMPLES

Synthetic Example 1: Synthesis of Compound of Chemical Formula 1

Synthetic Example 1-(1): Synthesis of Compound of Chemical Formula 1-a

As illustrated in the following Reaction Scheme 1, the compound of Chemical Formula 1-a was synthesized:

[Reaction Scheme 1]

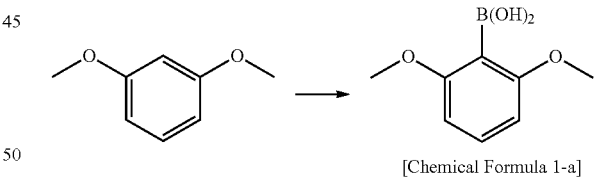

[Chemical Formula 1-a]

A dried 5-L reactor was charged with nitrogen. In the reactor, 1,3-dimethoxy benzene (200.0 g, 1.45 mol) and tetrahydrofuran (2000 ml) were placed. The solution was chilled to 0° C. in a nitrogen atmosphere and then added slowly with drops of 1.6 M n-butyl lithium (1085 ml, 1.74 mol). After 4 hrs of stirring at 0° C., the temperature was decreased to −78° C. Drops of trimethyl borate (225.6 g, 2.17 mol) were slowly added, followed by stirring for 12 hrs at room temperature.

After completion of the reaction, 2 M HCl (1000 ml) was dropwise added at room temperature and stirred for 30 min. Extraction was made with water and ethyl acetate, and the organic layer thus formed was concentrated in a vacuum and recrystallized in ethylacetate and hexane to afford the compound of Chemical Formula 1-a. (184 g, yield 70%).

(2) Synthesis of Compound of Chemical Formula 1-b

As illustrated in the following Reaction Scheme 2, the compound of Chemical Formula 1-b was synthesized:

[Reaction Scheme 2]

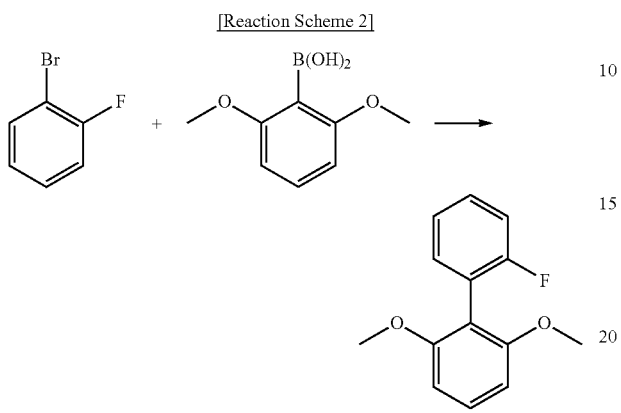

[Chemical Formula 1-a] [Chemical Formula 1-b]

The compound (183 g, 1006 mmol) of Chemical Formula 1-a obtained according to Reaction Scheme 1, 1-bromo-2-fluorobenzene (160 g, 914 mmol), tetrakis(triphenylphosphine)palladium (23.2 g, 20 mmol), potassium carbonate (252.7 g, 1829 mmol), 1,4-dioxane (800 ml), toluene (800 ml), and distilled water (320 ml) were placed and stirred together at 100° C. for 12 hrs.

After completion of the reaction, the reaction mixture was extracted with ethyl acetate and water. The organic layer thus formed was concentrated in a vacuum to afford the compound of Chemical Formula 1-b. (73.5 g, yield 34.5%)

(3) Synthesis of Compound of Chemical Formula 1-c

As illustrated in the following Reaction Scheme 3, the compound of Chemical Formula 1-c was synthesized:

[Reaction Scheme 3]

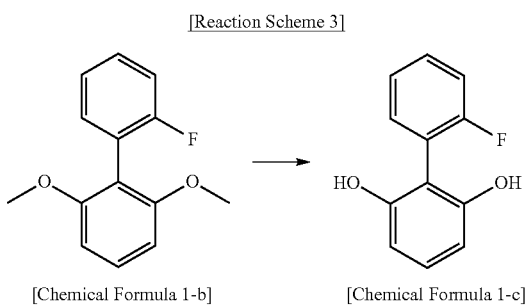

[Chemical Formula 1-b]   [Chemical Formula 1-c]

The compound (73.5 g, 316 mmol) of Chemical Formula 1-b obtained according to Reaction Scheme 2, bromic acid (122.9 g, 1519 mmol), and acetic acid (440 ml) were stirred for 12 hrs under reflux.

After completion of the reaction, the reaction mixture was extracted ethyl acetate and distilled water, and the organic layer thus formed was concentrated in a vacuum and isolated by column chromatography to afford the compound of Chemical Formula 1-c. (56.5 g, yield 87%)

(4) Synthesis of Compound of Chemical Formula 1-d

As illustrated in the following Reaction Scheme 4, the compound of Chemical Formula 1-d was synthesized:

[Reaction Scheme 4]

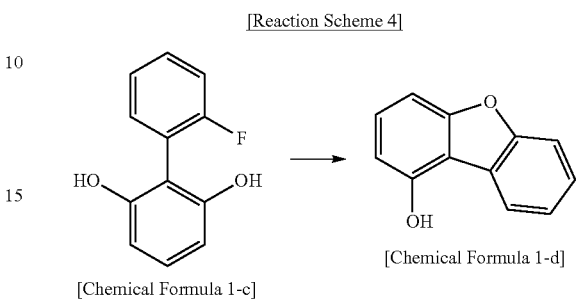

[Chemical Formula 1-c]   [Chemical Formula 1-d]

The compound (56.5 g, 277 mmol) of Chemical Formula 1-c obtained according to Reaction Scheme 3, and potassium carbonate (76.5 g, 553 mmol) were added to 1-methyl-2-pyrrolidinone (850 ml) and stirred for 2 hrs under reflux.

After completion of the reaction, the reaction mixture was acidified with 2 N HCl, concentrated, and extracted with methyl acetate and water. Recrystallization subsequent to filtration according the compound of Chemical Formula 1-d as a crystal. (25.0 g, yield 49%)

(5) Synthesis of Compound of Chemical Formula 1-e

As illustrated in the following Reaction Scheme 5, the compound of Chemical Formula 1-e was synthesized:

[Reaction Scheme 5]

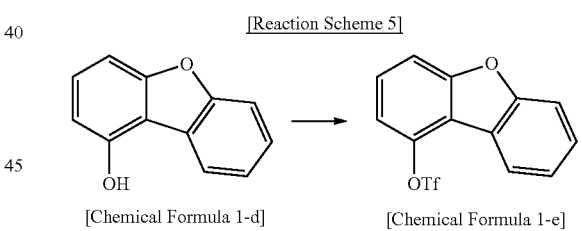

[Chemical Formula 1-d]   [Chemical Formula 1-e]

The compound (25 g, 136 mmol) of Chemical Formula 1-d and pyridine (21.5 g, 271 mmol) were added to methylene chloride (250 ml) and cooled to 0° C. Thereafter, drops of trifluoromethane sulfonyl anhydride (57.44 g, 204 mmol) were slowly added before stirring for 1 hrs.

After completion of the reaction, distilled water (200 ml) cooled to 5° C. were slowly added. Extraction with methylene chloride and distilled water was conducted, followed by recrystallization with methylene chloride and hexane to afford the compound of Chemical Formula 1-e. (35.0 g, yield 80%).

(6) Synthesis of Compound of Chemical Formula 1-f

As illustrated in the following Reaction Scheme 6, the compound of Chemical Formula 1-f was synthesized:

[Reaction Scheme 6]

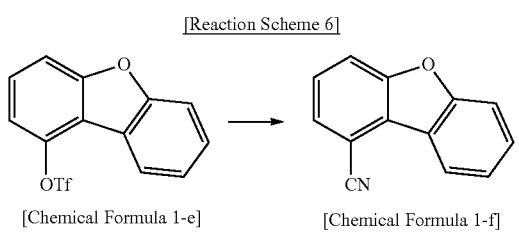 [SMILES: O=S(=O)(Oc1cccc2oc3ccccc3c12)C(F)(F)F ; N#Cc1cccc2oc3ccccc3c12]

[Chemical Formula 1-e]    [Chemical Formula 1-f]

The compound (35 g, 111 mmol) of Chemical Formula 1-e obtained according to Reaction Scheme 5, zinc cyanide (25.99 g, 221 mmol), and tetrakis(triphenylphosphine)palladium (5.12 g, 4 mmol) were added to dimethylformamide (380 ml) and stirred for 2 hrs under reflux.

After completion of the reaction, distilled water (100 ml) was dropwise added. The reaction mixture was filtered. The precipitate was dissolved in ethyl acetate and filtered through a celite pad. Recrystallization in methylene chloride and hexane afforded the compound of Chemical Formula 1-f as a crystal. (13 g, yield 60%)

(7) Synthesis of Compound of Chemical Formula 1-g

As illustrated in the following Reaction Scheme 7, the compound of Chemical Formula 1-g was synthesized:

[Reaction Scheme 7]

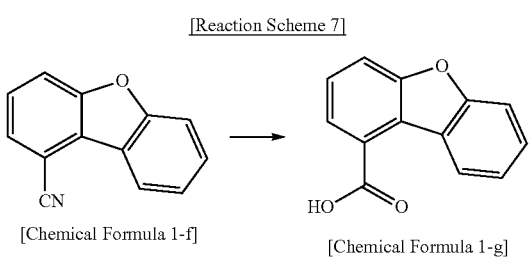 [SMILES: N#Cc1cccc2oc3ccccc3c12 ; O=C(O)c1cccc2oc3ccccc3c12]

[Chemical Formula 1-f]    [Chemical Formula 1-g]

The compound (13 g, 67 mmol) of Chemical Formula 1-f obtained according to Reaction Scheme 6 and potassium hydroxide (22.65 g, 404 mmol) were added to ethylene glycol (150 ml) and stirred for three days under reflux.

After completion of the reaction, 2 N HCl (500 ml) was dropwise added. The reaction mixture was filtered, and the precipitate thus formed was washed twice in methanol (200 ml) by stirring to afford the compound of Chemical Formula 1-g. (13 g, yield 91%)

(8) Synthesis of Compound of Chemical Formula 1-h

As illustrated in the following Reaction Scheme 8, the compound of Chemical Formula 1-h was synthesized:

[Reaction Scheme 8]

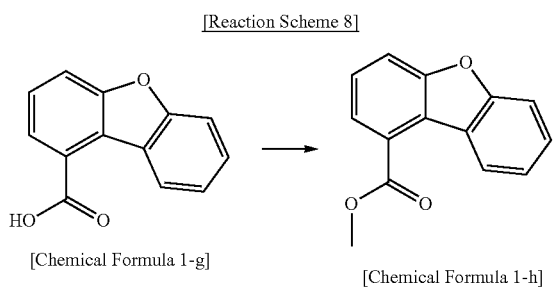 [SMILES: O=C(O)c1cccc2oc3ccccc3c12 ; COC(=O)c1cccc2oc3ccccc3c12]

[Chemical Formula 1-g]    [Chemical Formula 1-h]

The compound (13 g, 61 mmol) of Chemical Formula 1-g obtained according to Reaction Scheme 7, methanol (65 ml), and sulfuric acid (1.3 ml) were added to 1,4-dioxane (390 ml) and stirred for 24 hrs under reflux.

After completion of the reaction, the reaction mixture was concentrated, and extracted with methylene chloride and distilled water. The organic layer thus formed was concentrated, isolated by column chromatography, and crystallized in methanol (26 ml) to afford the compound of Chemical Formula 1-h as a crystal. (10.4 g, yield 75%)

(9) Synthesis of Compound of Chemical Formula 1-i

As illustrated in the following Reaction Scheme 9, the compound of Chemical Formula 1-i was synthesized:

[Reaction Scheme 9]

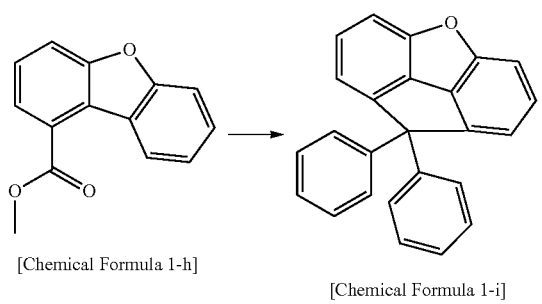

[Chemical Formula 1-h]    [Chemical Formula 1-i]

A dried, 250-mL reactor was charged with nitrogen and then with bromobenzene (18 g, 115 mmol) and tetrahydrofuran (180 ml), and cooled to −78° C. Drops of 1.6 M n-butyl lithium (72 ml, 115 mmol) were slowly added, followed by stirring at −78° C. for 1 hr. Subsequently, the compound (10.3 g, 46 mmol) of Chemical Formula 1-h obtained according to Reaction Scheme 8 was added, and the resulting mixture was heated to room temperature and stirred for 2 hrs.

After completion of the reaction, an aqueous solution (100 ml) was dropwise added at room temperature to the reaction mixture which was then stirred for 30 min. Extraction with ethyl acetate and water gave an organic layer which was then concentrated in a vacuum.

The concentrate was mixed with acetic acid (180 ml) and HCl (18 ml) at 70° C. for three days by stirring. After completion of the reaction, filtration in methanol afforded the compound of Chemical Formula 1-i. (6.8 g, yield 45%)

(10) Synthesis of Compound of Chemical Formula 1-j

As illustrated in the following Reaction Scheme 10, the compound of Chemical Formula 1-j was synthesized:

[Reaction Scheme 10]

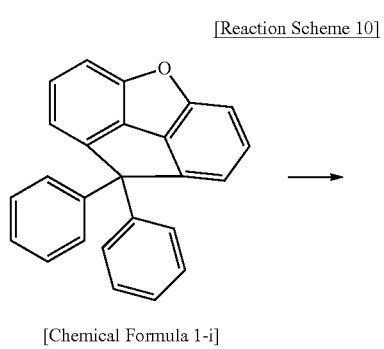

[Chemical Formula 1-i]

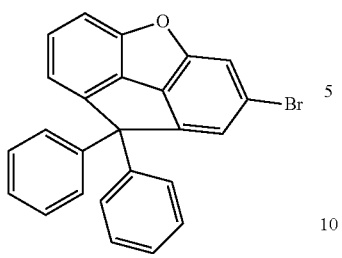

[Chemical Formula 1-j]

The compound (6.8 g, 20 mmol) of Chemical Formula 1-i obtained according to Reaction Scheme 9, methylene chloride (130 ml), and bromine (3.27 g, 20 mmol) were stirred together for 4 hrs.

After completion of the reaction, methanol (100 ml) was added for filtration. The precipitate thus formed was recrystallized in tetrahydrofuran to afford the compound of Chemical Formula 1-j. (6.6 g, yield 78%)

(11) Synthesis of Compound of Chemical Formula 1

As illustrated in the following Reaction Scheme 11, the compound of Chemical Formula 1 was synthesized:

[Reaction Scheme 11]

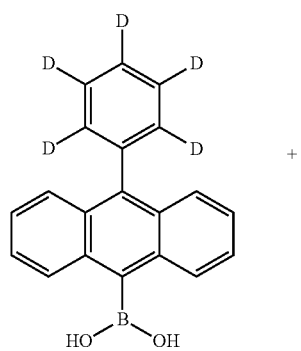

+

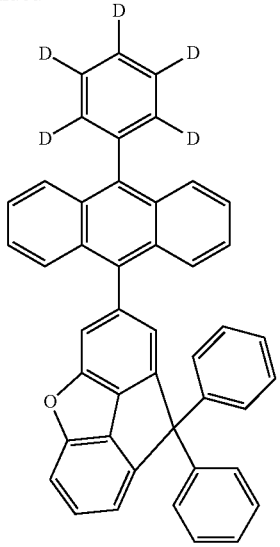

[Chemical Formula 1]

The compound (6.6 g, 14 mmol) of Chemical Formula 1-j obtained according to Reaction Scheme 10, phenyl anthracene boronic acid (5.4 g, 18 mmol), tetrakis(triphenylphosphine)palladium (0.42 g, 0.3 mmol), potassium carbonate (4.92 g, 36 mmol), 1,4-dioxane (30 ml), toluene (30 ml), and distilled water (120 ml) were stirred together at 100° C. for 12 hrs.

After completion of the reaction, the reaction mixture was extracted with methylene chloride and distilled water. The organic layer was concentrated, isolated through column chromatography, and recrystallized twice in methylene chloride and acetone to afford the compound of Chemical Formula 1. (1.4 g, yield 13%)

Example 2

Synthesis Example 2: Synthesis of Compound of Chemical Formula 22

(1) Synthe Example 2-(1): Synthesis of Compound of Chemical Formula 2-a

As illustrated in the following Reaction Scheme 12, the compound of Chemical Formula 2-a was synthesized:

[Reaction Scheme 12]

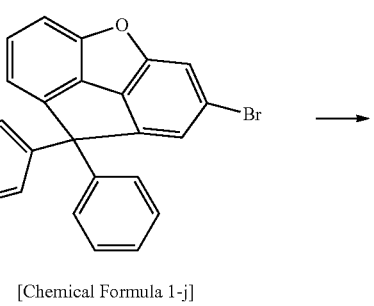

[Chemical Formula 1-j]

→

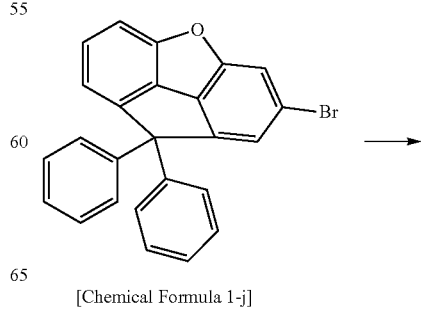

[Chemical Formula 1-j]

→

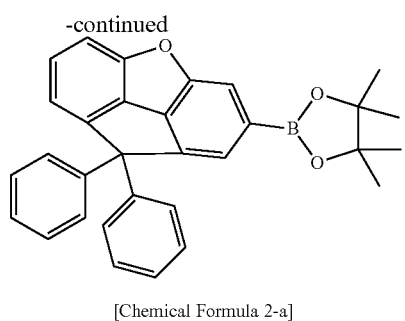

[Chemical Formula 2-a]

The compound (6.6 g, 0.016 mol) of Chemical Formula 1-j obtained according to Reaction Scheme 10, bis(pinacolato)diboron (4.87 g, 0.019 mol), 1,1'-bis(diphenylphosphino)ferocene-palladium(II) dichloride (0.26 g, 0.001 mol), potassium acetate (3.15 g, 0.032 mol), and toluene (70 ml) were stirred together overnight under reflux. After completion of the reaction, the reaction mixture was filtered through a celite pad and concentrated in a vacuum. Purification through column chromatography afforded the compound of Chemical Formula 2-a. (5.2 g, 70.7%)

(2) Synthe Example 2-(2): Synthesis of Compound of Chemical Formula 2-b

As illustrated in the following Reaction Scheme 13, the compound of Chemical Formula 2-b was synthesized:

[Reaction Scheme 13]

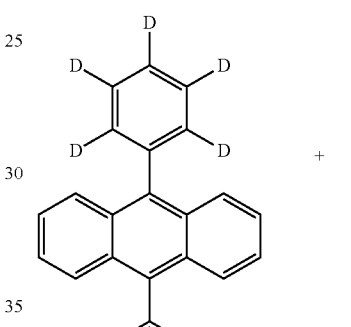

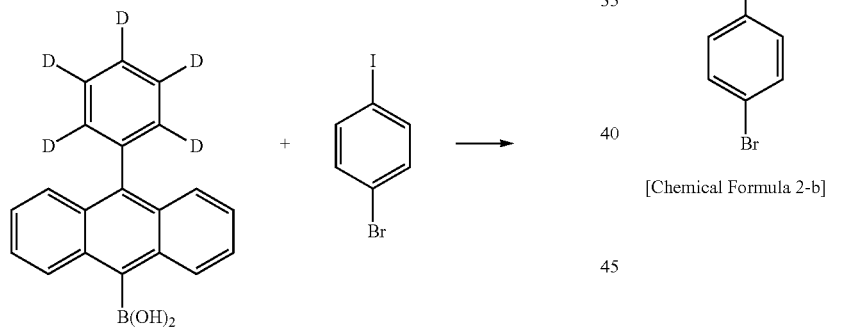

[Chemical Formula 2-b]

In a reactor, (10-phenyl(d5)-anthracene-9-boronic acid (38.6 g, 127 mmol), 1-bromo-4-iodobenzene (30.0 g, 106 mmol), tetrakis(triphenylphosphine)palladium (3.43 g, 3 mmol), and potassium carbonate (27.35 g, 197.9 mmol) were placed, followed by toluene (150 mL), tetrahydrofuran (150 mL), and water (60 mL). The mixture was heated to 90° C. and stirred overnight. After completion of the reaction, the temperature of the reactor was cooled to room temperature and the reaction mixture was extracted with ethyl acetate. Purification through column chromatography afforded the compound of Chemical Formula 2-b. (35.0 g, yield 79.7%)

(3) Synthe Example 2-(3): Synthesis of Compound of Chemical Formula 22

As illustrated in the following Reaction Scheme 14, the compound of Chemical Formula 22 was synthesized:

[Reaction Scheme 14]

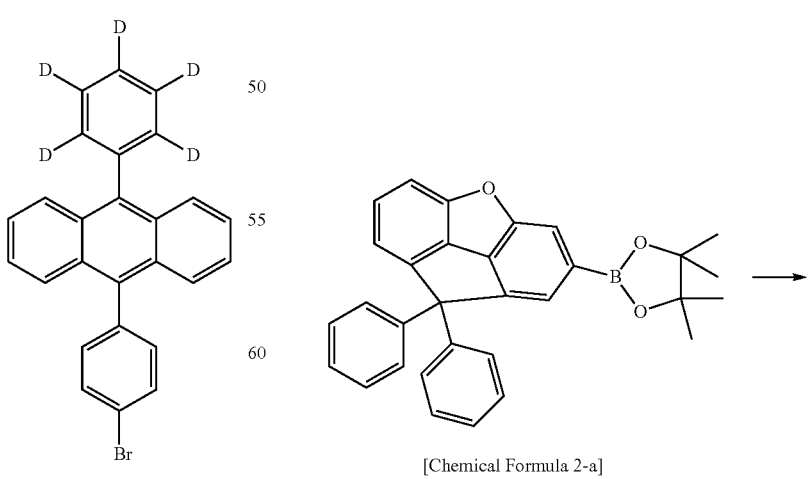

[Chemical Formula 2-b]

[Chemical Formula 2-a]

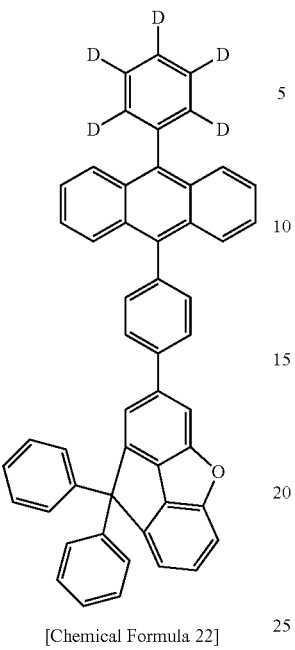

[Chemical Formula 22]

In a reactor, the compound (5 g, 0.012 mol) of Chemical Formula 2-a obtained according to Reaction Scheme 12, the compound (6.64 g, 0.014 mol) of Chemical Formula 2-b obtained according to Reaction Scheme 13, tetrakis(triphenylphosphine)palladium (0.28 g, 0.001 mol), and potassium carbonate (3.34 g, 0.024 mol) were placed, followed by toluene (25 mL), tetrahydrofuran (25 mL), and water (10 mL). The temperature of the reactor was elevated to 80° C. and the mixture was stirred overnight. After completion of the reaction, the temperature of the reactor was cooled to room temperature, and the reaction mixture was extracted with ethyl acetate and concentrated in a vacuum. The concentrate was purified through column chromatography and recrystallized in toluene and acetone to afford the compound of Chemical Formula 22. (3 g, 37.3%)

Example 3

Synthesis Example 3: Synthesis of Compound of Chemical Formula 3

(1) Synthesis Example 3-(1): Synthesis of Compound of Chemical Formula 3-a

As illustrated in the following Reaction Scheme 15, the compound of Chemical Formula 3-a was synthesized:

[Reaction Scheme 15]

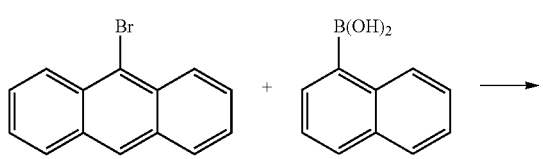

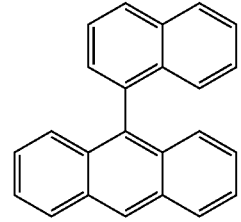

<Chemical Formula 3-a>

In a 2-L reactor, 9-bromoanthracene (17 g, 41 mmol), 1-naphthalene bromic acid (8.4 g, 41 mmol), tetrakis(triphenylphosphine)palladium (0.95 g, 0.82 mmol), potassium carbonate (17 g, 123 mmol), 1,4-dioxane (80 mL), toluene (80 mL), and distilled water (40 mL) were placed, and stirred for 12 hrs under reflux. The reaction mixture was cooled to room temperature, followed by layer separation. The organic layer was concentrated in a vacuum and purified through column chromatography to afford the compound of Chemical Formula 3-a. (15 g, yield 90%)

(2) Synthesis Example 3-(2): Synthesis of Compound of Chemical Formula 3-b

As illustrated in the following Reaction Scheme 16, the compound of Chemical Formula 3-b was synthesized:

[Reaction Scheme 16]

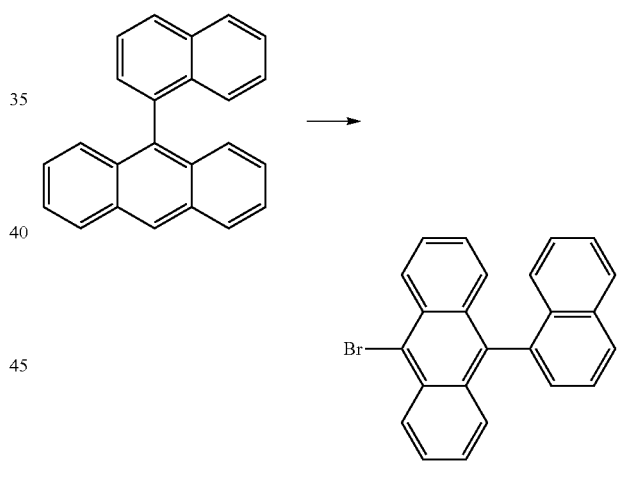

<Chemical Formula 3-b>

The compound (50 g, 205 mmol) of Chemical Formula 3-a obtained according to Reaction Scheme 15 and dimethylformamide (500 mL) were stirred together. N-bromosuccinimide (36.5 g, 205 mmol) was divisionally added as a solid to the reactor, followed by stirring at room temperature for 3 hrs. The reaction mixture was poured to an excess of H2O to form precipitates which were then filtered. The precipitates were slurried in methanol, filtered, and dried to afford the compound of Chemical Formula 3-b. (60.7 g, yield 92%)

(3) Synthesis Example 3-(3): Synthesis of Compound of Chemical Formula 3-c

As illustrated in the following Reaction Scheme 17, the compound of Chemical Formula 3-c was synthesized:

[Reaction Scheme 17]

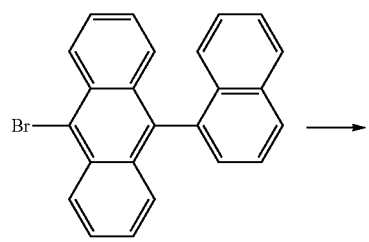

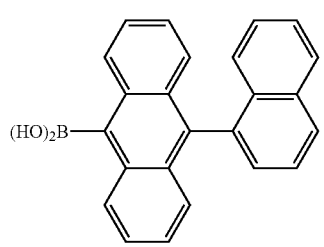

<Chemical Formula 3-c>

In a reactor, the compound (50 g, 271 mmol) of Chemical Formula 3-b obtained according to Reaction Scheme 16 and tetrahydrofuran (500 mL) were cooled to −78° C. under a nitrogen atmosphere. After 30 min, drops of 1.6 M n-butyl lithium (203 mL, 325 mmol) were slowly added and stirred at −78° C. for 1 hr. Drops of trimethyl borate (33.8 g, 325 mmol) were slowly added at −78° C. and stirred at room temperature for 2 hrs. An aqueous 2 M HCl solution was added and stirred. The reaction mixture was extracted with ethyl acetate and H2O and the organic layer was concentrated in a vacuum. Recrystallization in heptane afforded the compound of Chemical Formula 3-c. (51 g, yield 83%)

(4) Synthesis Example 3-(4): Synthesis of Compound of Chemical Formula 3-d

As illustrated in the following Reaction Scheme 18, the compound of Chemical Formula 3-d was synthesized:

[Reaction Scheme 18]

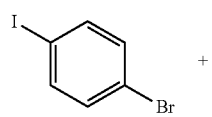

+

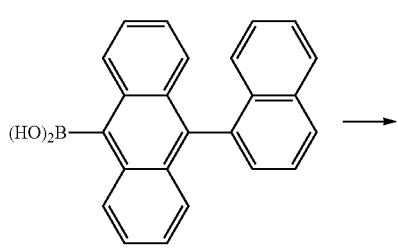

<Chemical Formula 3-d>

The same procedure was carried out as in Reaction Scheme 13, with the exception of using the compound of Chemical Formula 3-c instead of (10-phenyl(d5)-anthracene-9-boronic acid, to synthesize the compound of Chemical Formula 3-d. (10.5 g, yield 74.1%)

(5) Synthesis Example 3-(5): Synthesis of Compound of Chemical Formula 3

As illustrated in the following Reaction Scheme 19, the compound of Chemical Formula 3 was synthesized:

[Reaction Scheme 19]

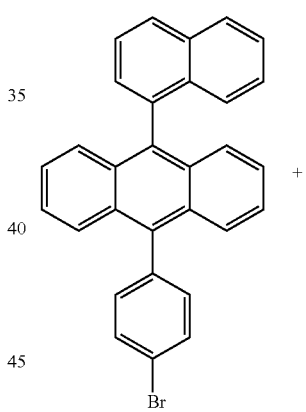

[Chemical Formula 3-d]

+

[Chemical Formula 2-a]

47
-continued

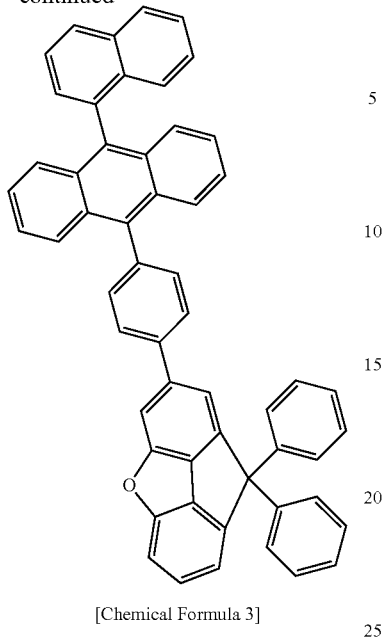

[Chemical Formula 3]

The same procedure was carried out as in Reaction Scheme: 14, with the exception of using the compound of Chemical Formula 3-d instead of the compound of Chemical Formula 2-b, to synthesize the compound of Chemical Formula 3. (4.0 g, yield 57.2%)

Example 4

Synthesis Example 4: Synthesis of Compound of Chemical Formula 23

(1) Synthesis Example 4-(1): Synthesis of Compound of Chemical Formula 4-a

As illustrated in the following Reaction Scheme 20, the compound of Chemical Formula 4-a was synthesized:

[Reaction Scheme 20]

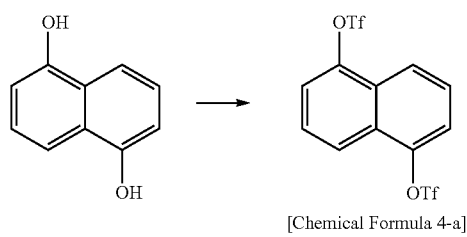

[Chemical Formula 4-a]

In a 2-L reactor, 1,5-dihydroxy naphthalene (60.0 g, 0.75 mol) was dissolved in methylene chloride (600 ml) to which pyridine (88.99 g, 1.125 mol) was then slowly added, followed by stirring at room temperature for 30 min. The reaction mixture was cooled to 0° C. and slowly added with drops of trifluoromethanesulfonyl anhydride (253.92 g, 0.900 mol) at the same temperature. Afterward, the reaction mixture was stirred at room temperature for 5 hrs, slowly added with water (100 ml), and stirred again for 10 min. Extraction with water and ethyl acetate was conducted before concentration in a vacuum. The concentrate was purified through column chromatography to afford the compound of Chemical Formula 4-a. (140 g, 88.0%)

48

(2) Synthesis Example 4-(2): Synthesis of Compound of Chemical Formula 4-b

As illustrated in the following Reaction Scheme 21, the compound of Chemical Formula 4-b was synthesized:

[Reaction Scheme 21]

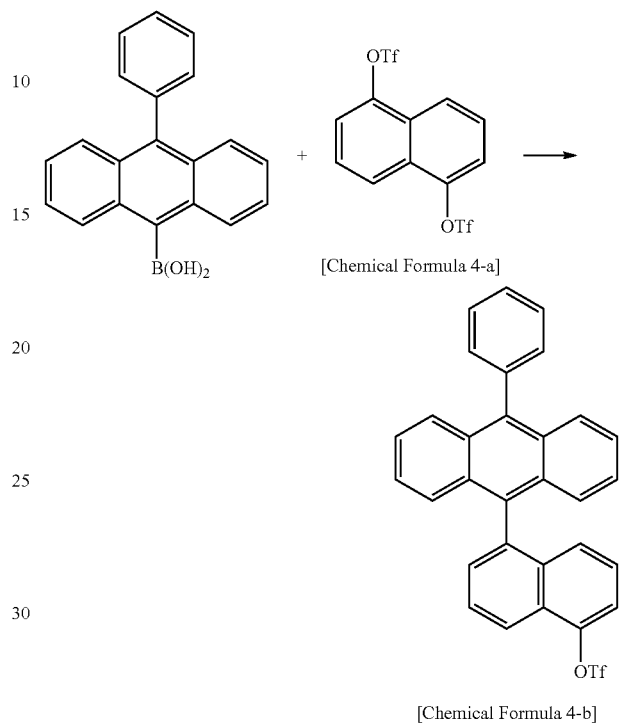

[Chemical Formula 4-b]

The same procedure was carried out as in Reaction Scheme 14, with the exception of using the compound of Chemical Formula 4-a and phenyl anthracene boronic acid instead of the compound of Chemical Formula 2-b and the compound of Chemical Formula 2-a, respectively, to synthesize the compound of Chemical Formula 4-b. (40 g, yield 63%)

(3) Synthesis Example 4-(2): Synthesis of Compound of Chemical Formula 23

As illustrated in the following Reaction Scheme 22, the compound of Chemical Formula 23 was synthesized:

[Reaction Scheme 23]

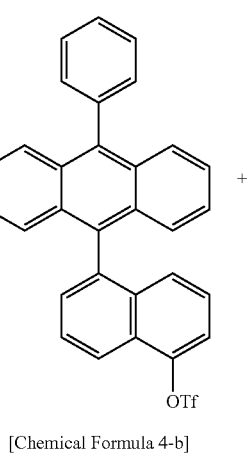

[Chemical Formula 4-b]

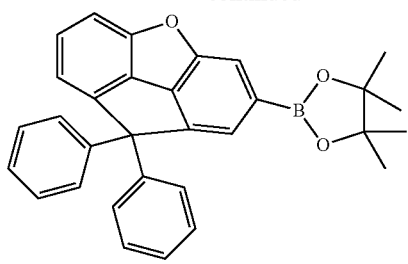

[Chemical Formula 1-j]

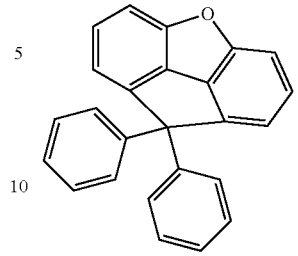

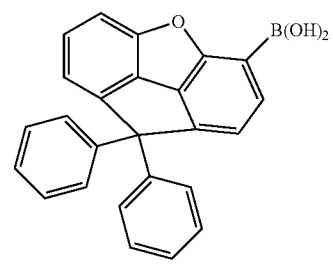

[Chemical Formula 5-a]

[Reaction Scheme 23]

In a well dried, 2-L reactor, the compound (100.0 g, 0.301 mol) of Chemical Formula 1-i obtained according to Reaction Scheme 9 was dissolved in tetrahydrofuran (800 ml). The solution was cooled to −78° C. in a nitrogen atmosphere and slowly added with drops of 1.6 M n-butyl lithium (225 ml, 0.361 mol). At the same temperature, stirring was continued for 4 hrs. Drops of trimethylborate (43.7 g, 0.421 mol) was slowly added over 30 min, followed by stirring overnight at room temperature. After completion of the reaction, 2 N HCl was slowly added for acidification. The reaction mixture was extracted with water and ethyl acetate. The organic layer thus formed was dried over magnesium sulfate, concentrated in a vacuum, and recrystallized in heptane to afford the compound of Chemical Formula 5-a. (90.0 g, yield 79.5%)

(3) Synthesis Example 5-(2): Synthesis of Compound of Chemical Formula 24

As illustrated in the following Reaction Scheme 24, the compound of Chemical Formula 24 was synthesized:

[Reaction Scheme 24]

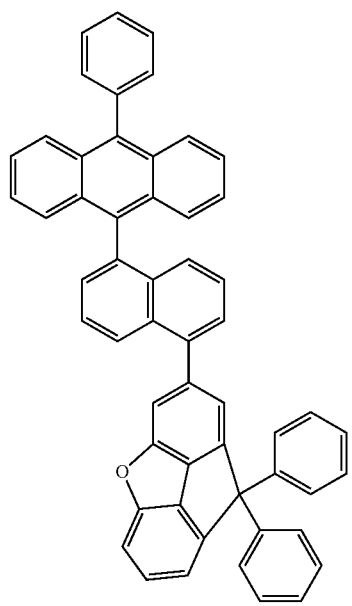

[Chemical Formula 23]

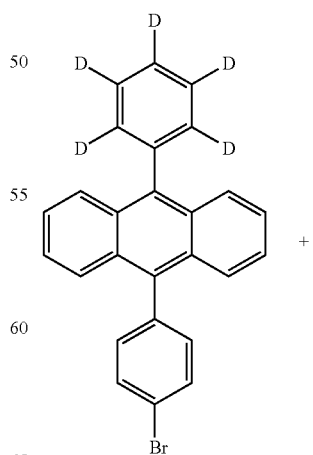

[Chemical Formula 2-b]

The same procedure was carried out as in Reaction Scheme 14, with the exception of using the compound of Chemical Formula 4-b and the compound of Chemical Formula 1-j instead of the compound of Chemical Formula 2-b and the compound of Chemical Formula 2-a, respectively, to synthesize the compound of Chemical Formula 23. (4 g, yield 37.2%)

Example 5

Synthesis Example 5: Synthesis of Compound of Chemical Formula 24

(1) Synthesis Example 5-(1): Synthesis of Compound of Chemical Formula 5-a

As illustrated in the following Reaction Scheme 23, the compound of Chemical Formula 5-a was synthesized:

-continued

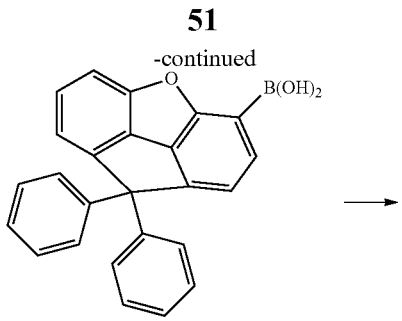

[Chemical Formula 5-a]

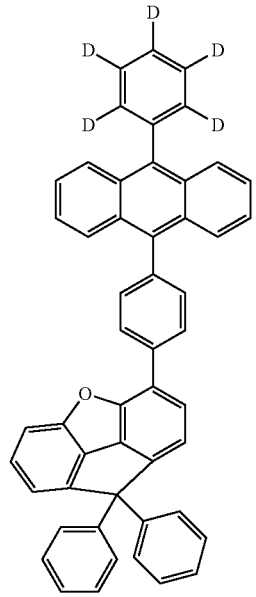

[Chemical Formula 24]

The same procedure was carried out as in Reaction Scheme 14, with the exception of using the compound of Chemical Formula 5-a instead of the compound of Chemical Formula 2-a, to synthesize the compound of Chemical Formula 24. (3.1 g, yield 42.3%)

Example 6

Synthesis Example 6: Synthesis of Compound of Chemical Formula 10

(1) Synthesis Example 6-(1): Synthesis of Compound of Chemical Formula 6-a

As illustrated in the following Reaction Scheme 25, the compound of Chemical Formula 6-a was synthesized:

[Reaction Scheme 25]

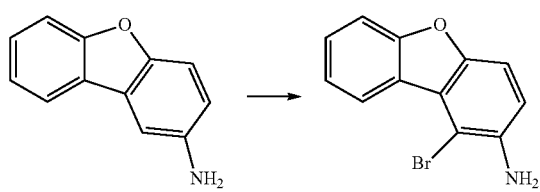

[Chemical Formula 6-a]

In a reactor, 2-aminodibenzofuran (52.0 g, 284 mmol), acetic acid (1000 ml), sodium carbonate (27 g, 255 mmol), and bromine (43.09 g, 270 mmol) were placed and stirred together for 2 hrs. After completion of the reaction, methanol (1000 ml) was added for filtration. Purification through column chromatography afforded the compound of Chemical Formula 6-a. (17.6 g, yield 26.9%)

(2) Synthesis Example 6-(2): Synthesis of Compound of Chemical Formula 6-b

As illustrated in the following Reaction Scheme 26, the compound of Chemical Formula 6-b was synthesized:

[Reaction Scheme 26]

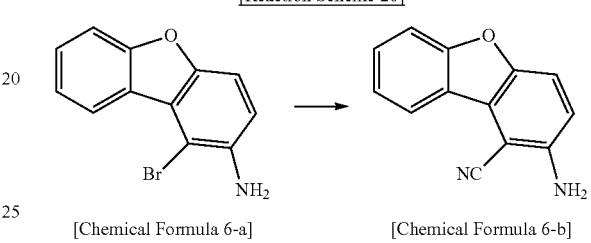

[Chemical Formula 6-a]  [Chemical Formula 6-b]

The compound (20 g, 76 mmol) of Chemical Formula 6-a obtained according to Reaction Scheme 25, zinc cyanide (17.93 g, 153 mmol), and tetrakis(triphenylphosphine)palladium (3.53 g, 3 mmol) were dissolved in dimethylformamide (200 ml) and refluxed for 2 hrs. After completion of the reaction, distilled water (100 ml) was added and the reaction mixture was filtered. The solid thus obtained was dissolved in ethyl acetate and filtered through a celite pad. Recrystallization in methylene chloride and hexane afforded the compound of Chemical Formula 6-b. (13 g, yield 81.8%)

(3) Synthesis Example 6-(3): Synthesis of Compound of Chemical Formula 6-c

As illustrated in the following Reaction Scheme 27, the compound of Chemical Formula 6-c was synthesized:

[Reaction Scheme 27]

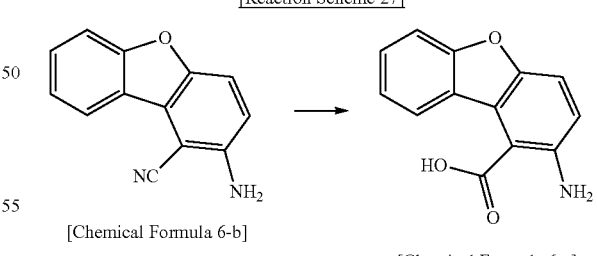

[Chemical Formula 6-b]  [Chemical Formula 6-c]

The compound (13 g, 62 mmol) of Chemical Formula 6-b obtained according to Reaction Scheme 26, potassium hydroxide (21.02 g, 375 mmol), and ethylene glycol (150 ml) were stirred together for 3 days under reflux. After completion of the reaction, 2N HCl (500 ml) was dropwise added. Filtration gave a solid which was washed twice with methanol (200 ml) to afford the compound of Chemical Formula 6-c. (12 g, yield 84.6%).

(4) Synthesis Example 6-(4): Synthesis of Compound of Chemical Formula 6-d

As illustrated in the following Reaction Scheme 28, the compound of Chemical Formula 6-d was synthesized:

[Reaction Scheme 28]

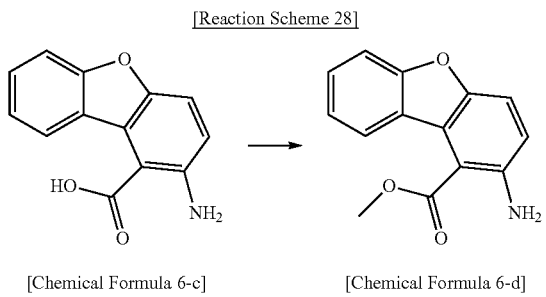 [SMILES: Nc1ccc2oc3ccccc3c2c1C(=O)O ; COC(=O)c1c(N)ccc2oc3ccccc3c12]

[Chemical Formula 6-c]   [Chemical Formula 6-d]

The compound (12 g, 57 mmol) of Chemical Formula 6-c obtained according to Reaction Scheme 27, methanol (60 ml), sulfuric acid (1.2 ml), and 1,4-dioxane (360 ml) were stirred together for 24 hrs under reflux. After completion of the reaction, the reaction mixture was concentrated, and extracted with methylene chloride and distilled water. Subsequent to purification through column chromatography, recrystallization in methanol afforded the compound of Chemical Formula 6-d. (11.4 g, yield 89.1%)

(5) Synthesis Example 6-(5): Synthesis of Compound of Chemical Formula 6-e

As illustrated in the following Reaction Scheme 29, the compound of Chemical Formula 6-e was synthesized:

[Reaction Scheme 29]

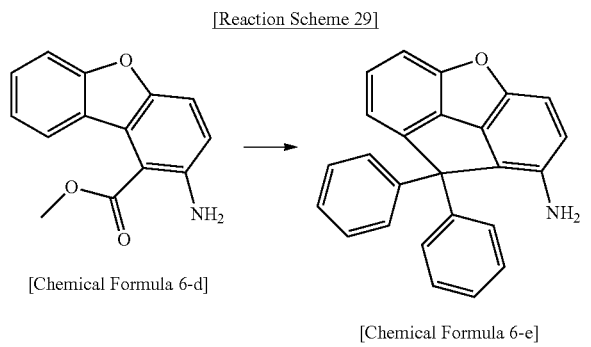 [SMILES: COC(=O)c1c(N)ccc2oc3ccccc3c12 ; Nc1ccc2oc3cccc4c3c2c1C4(c1ccccc1)c1ccccc1]

[Chemical Formula 6-d]

[Chemical Formula 6-e]

A dried 250-mL reactor was charged with nitrogen. In the reactor, bromobenzene (18 g, 115 mmol) and tetrahydrofuran (180 ml) were placed, cooled to −78° C., and slowly added with drops of 1.6M n-butyl lithium (72 ml, 115 mmol), followed by stirring for 1 hr. The compound (11.06 g, 46 mmol) of Chemical Formula 6-d obtained according to Reaction Scheme 28 was added and then stirred at room temperature for 2 hrs. After completion of the reaction, an aqueous solution (100 ml) was dropwise added and stirred for 30 min. Then, the reaction mixture was extracted with ethyl acetate and water and the organic layer was concentrated in a vacuum. The concentrate was added with acetic acid (180 ml) and HCl (18 ml) and stirred at 70° C. for three days. After completion of the reaction, filtration in methanol afforded the compound of Chemical Formula 6-e. (9.5 g, yield 59.8%)

(6) Synthesis Example 6-(6): Synthesis of Compound of Chemical Formula 6-f

As illustrated in the following Reaction Scheme 30, the compound of Chemical Formula 6-f was synthesized:

[Reaction Scheme 30]

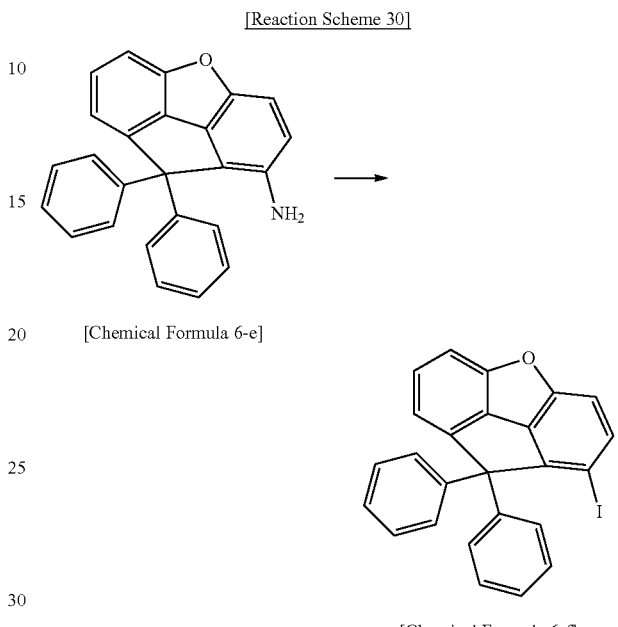

[Chemical Formula 6-e]

[Chemical Formula 6-f]

A mixture of the compound (10 g, 29 mmol) of Chemical Formula 6-e obtained according to Reaction Scheme 29, water (100 ml), and HCl (15 ml) was cooled to 0° C. A solution of sodium nitrile (2.38 g, 35 mmol) in water (10 ml) was slowly added to the mixture which was then stirred at 0° C. for 30 min. A solution of potassium iodine (9.56 g, 58 mmol) in water (15 ml) was slowly added, followed by stirring for 4 hrs. After completion of the reaction, the reaction mixture was extracted with sodium thiosulfate and ethyl acetate. Purification through column chromatography afforded the compound of Chemical Formula 6-f. (5.4 g, yield 40.9%)

(7) Synthesis Example 6-(7): Synthesis of Compound of Chemical Formula 6-g

As illustrated in the following Reaction Scheme 31, the compound of Chemical Formula 6-g was synthesized:

[Reaction Scheme 31]

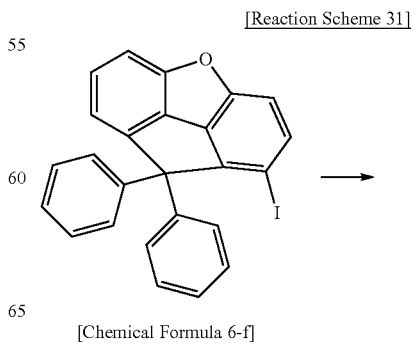

[Chemical Formula 6-f]

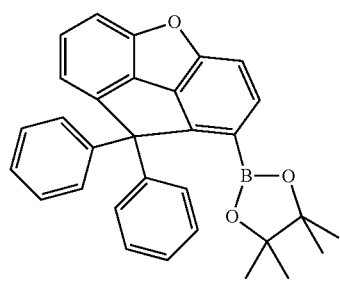

[Chemical Formula 6-g]

The same procedure was carried out as in Reaction Scheme 12, with the exception of using the compound of Chemical Formula 6-f instead of the compound of Chemical Formula 1-j, to synthesize the compound of Chemical Formula 6-g. (3.2 g, yield 62%)

(8) Synthesis Example 6-(8): Synthesis of Compound of Chemical Formula 6-h

As illustrated in the following Reaction Scheme 32, the compound of Chemical Formula 6-h was synthesized:

[Reaction Scheme 32]

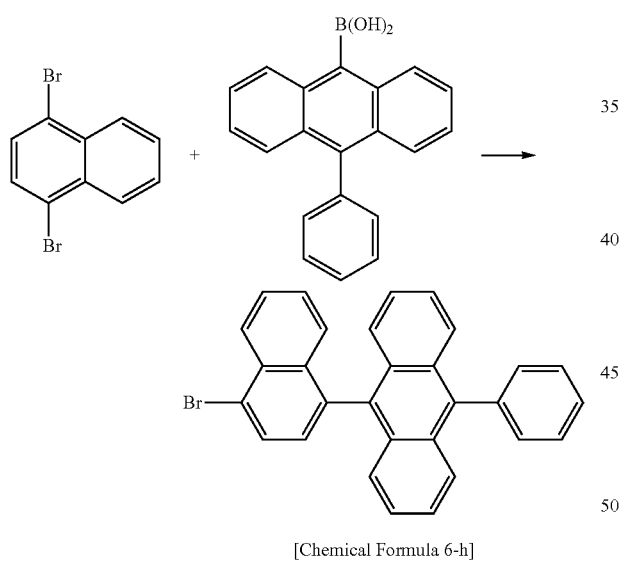

[Chemical Formula 6-h]

The same procedure was carried out as in Reaction Scheme 14, with the exception of using 1,4-dibromonaphthalene and phenyl anthracene boronic acid instead of the compound of Chemical Formula 2-b and the compound of Chemical Formula 2-a, respectively, to synthesize the compound of Chemical Formula 6-h. (28.5 g, yield 84.3%)

(9) Synthesis Example 6-(9): Synthesis of Compound of Chemical Formula 10

As illustrated in the following Reaction Scheme 33, the compound of Chemical Formula 10 was synthesized:

[Reaction Scheme 33]

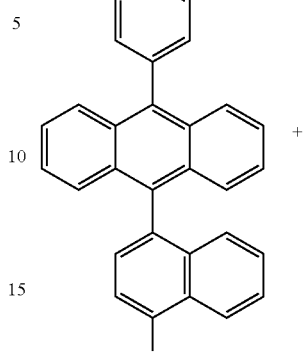

[Chemical Formula 6-h]

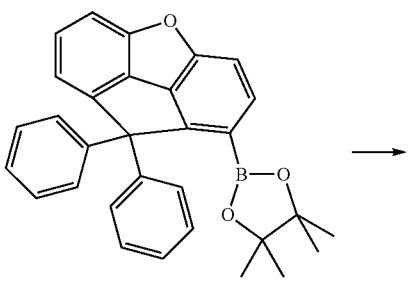

[Chemical Formula 6-g]

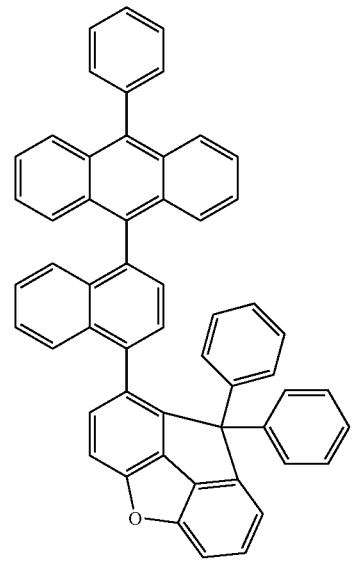

[Chemical Formula 10]

The same procedure was carried out as in Reaction Scheme 14, with the exception of using the compound of Chemical Formula 6-h and the compound of Chemical Formula 6-g instead of the compound of Chemical Formula 2-b and the compound of Chemical Formula 2-a, respectively, to synthesize the compound of Chemical Formula 10. (1.7 g, yield 42.3%)

Example

1. Fabrication of OLED

An ITO glass substrate was patterned to have a translucent area of 2 mm×2 mm and cleansed. The ITO glass was mounted in a vacuum chamber that was then set to have a base pressure of $1\times10^{-6}$ torr. On the ITO glass substrate, films were formed of DNTPD (700 Å), NPD (300 Å), the host compounds of the present disclosure, listed in Table 1, below+BD1 (5%) (300 Å), [Chemical Formula E-1]:[Chemical Formula E-2]=1:1, [Chemical Formula E-1] (5 Å), and Al (1,000 Å) in that order. The OLEDs thus obtained were measured at 0.4 mA for luminescence properties. Structures of DNTPD, α-NPD, [Chemical Formula E-1], [Chemical Formula E-2], and [BD 1] are as follows:

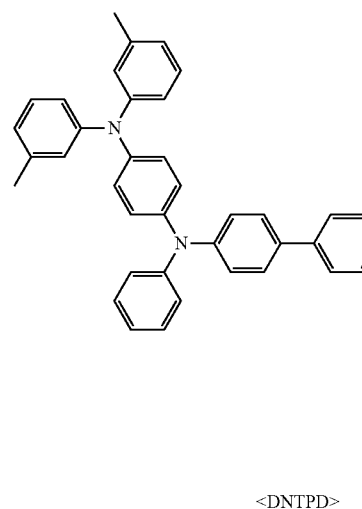

<DNTPD>

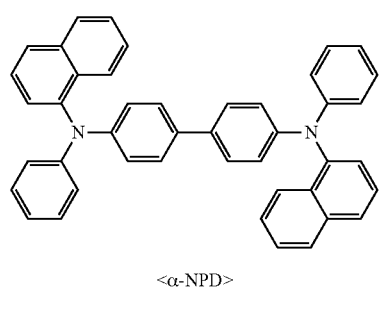

<α-NPD>

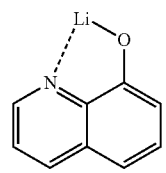

<Chemical Formula E-1>

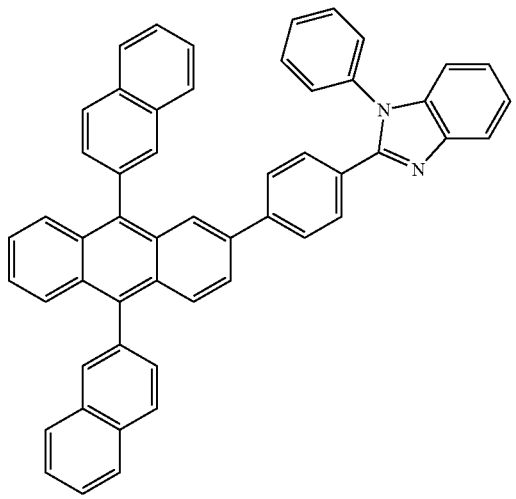

<Chemical Formula E-2>

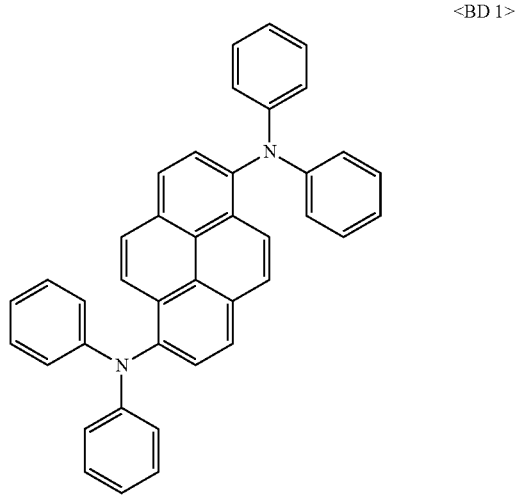 [SMILES: c1ccc(N(c2ccccc2)c2ccc3ccc4c(N(c5ccccc5)c5ccccc5)ccc5ccc2c3c54)cc1]

<BD 1>

Comparative Example 1

An OLED was fabricated in the same manner as in Examples 1 to 6, with the exception that [BH1] was used instead of the compounds used in Examples 1 to 6. The structure of [BH1] is as follows:

[BH1]

The OLEDs fabricated in the Examples and Comparative Example were measured for voltage, luminance, color coordinates, and lifespan, and the results are summarized in Table 1, below. For voltage, luminance and color coordinates, measurement was made at a current density of 10 mA/cm$^2$.

TABLE 1

| Host | | Luminance (Cd/m2) | CIEx | CIEy |
|---|---|---|---|---|
| Example 1 | Chemical Formula 1 | .2 | 510 | 0.139 | 0.12 |
| Example 2 | Chemical Formula 22 | .2 | 550 | 0.138 | 0.12 |
| Example 3 | Chemical Formula 3 | .2 | 570 | 0.138 | 0.12 |
| Example 4 | Chemical Formula 23 | .2 | 500 | 0.138 | 0.12 |
| Example 5 | Chemical Formula 24 | .2 | 600 | 0.139 | 0.12 |
| Example 6 | Chemical Formula 10 | .2 | 520 | 0.138 | 0.12 |
| C. Example 1 | BH 1 | .2 | 420 | 0.139 | 0.12 |

When used in OLEDs, as is understood from the data of Table 1, the novel compounds according to embodiments of the present disclosure exhibits outstanding luminance, thus imparting improved performance to the OLEDs.

INDUSTRIAL APPLICABILITY

The present disclosure is industrially applicable as it allows for the fabrication of OLEDs that exhibit the diode properties of high stability and efficiency.

The invention claimed is:

1. An organic luminescent compound, represented by the following Chemical Formula A:

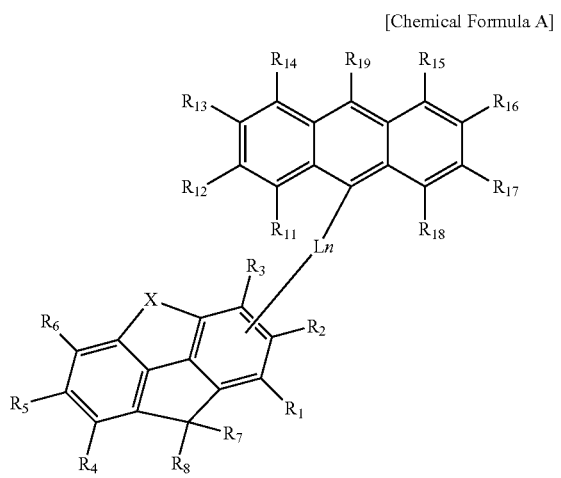

[Chemical Formula A]

wherein,
X is O or S,
one of R1 to R3 is a single bond connected to linker L;
R1 to R8, and R11 to R19 may be same or different, and are each independently selected from among a hydrogen atom, a deuterium atom, a substituted or unsubstituted alkyl of 1 to 40 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms bearing at least one selected from among O, N, S, and Si as a heteroatom, a substituted or unsubstituted alkoxy of 1 to 30 carbon atoms, a substituted or unsubstituted aryloxy of 6 to 30 carbon atoms, a substituted or unsubstituted alkylthio of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, a substituted or unsubstituted arylsilyl of 6 to 30 carbon atoms, a cyano, a nitro, and a halogen, with a proviso that R1 to R8, and R11 to R19 may each be connected to an adjacent radical thereof to form an aliphatic or aromatic mono- or polycyclic ring which may bear at least one selected from N, S, and O as a heteroatom;

the linker L is a single bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, or a substituted or unsubstituted heteroarylene of 2 to 60 carbon atoms; and n is an integer of 1 to 3, with a proviso that when n is 2 or greater, corresponding L's may be same or different, wherein the term 'substituted' in the expression 'substituted or unsubstituted' used in Chemical Formula A means having at least one substituent selected from the group consisting of a deuterium, a cyano, a halogen, a hydroxy, a nitro, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, a heteroarylamino of 1 to 24 carbon atoms, an alkylsilyl of 1 to 24 carbon atoms, an arylsilyl of 6 to 24 carbon atoms, and an aryloxy of 6 to 24 carbon atoms.

2. The organic luminescent compound as set forth in claim 1, wherein the linker L is a single bond or one selected from among compounds represented by the following Structural Formulas 1 to 9, and n is 1 or 2:

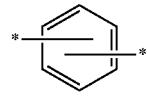

[Structural Formula 1]

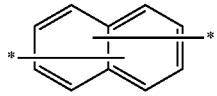

[Structural Formula 2]

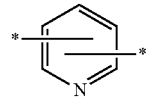

[Structural Formula 3]

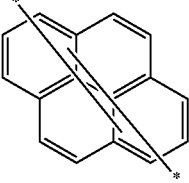

[Structural Formula 4]

61

-continued

[Structural Formula 5]

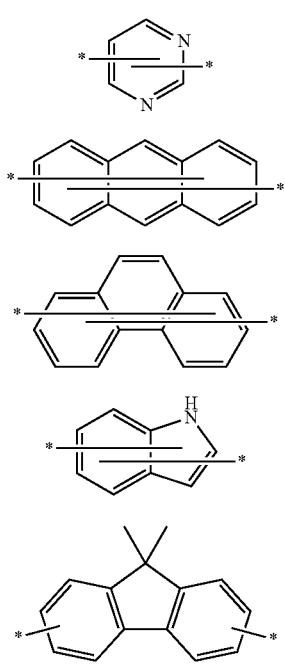

[Structural Formula 6]

[Structural Formula 7]

[Structural Formula 8]

[Structural Formula 9]

wherein each of the unsubstituted carbon atoms of the aromatic ring moiety may be bound with a hydrogen atom or a deuterium atom.

3. The organic luminescent compound as set forth in claim 2, wherein the substituents R7 and R8 bond to each other to form a ring.

4. The organic luminescent compound as set forth in claim 2, wherein adjacent two of the substituents R4 to R8 bond to each other to form a ring.

5. The organic luminescent compound as set forth in claim 1, wherein the substituent R19 in Chemical Formula A is a substituted or unsubstituted aryl of 6 to 24 carbon atoms.

6. The organic luminescent compound as set forth in claim 1, wherein L is a single bond or the compound of the following Structural Formula 1 or 2, and n is 1:

[Structural Formula 1]

[Structural Formula 2]

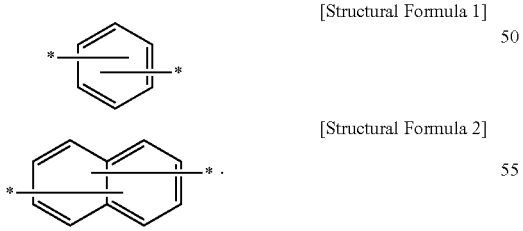

7. The organic luminescent compound as set forth in claim 6, wherein the substituents R7 and R8 are each a substituted or unsubstituted aryl of 6 to 24 carbon atoms.

8. The organic luminescent compound as set forth in claim 1, wherein the substituent R19 in Chemical Formula A is a substituted or unsubstituted aryl of 6 to 24 carbon atoms bearing a deuterium atom on the aromatic ring thereof.

62

9. The organic luminescent compound as set forth in claim 1, wherein the organic luminescent compound is any one selected from among compounds represented by the following Chemical Formulas 1 to 24:

<Chemical Formula 1>

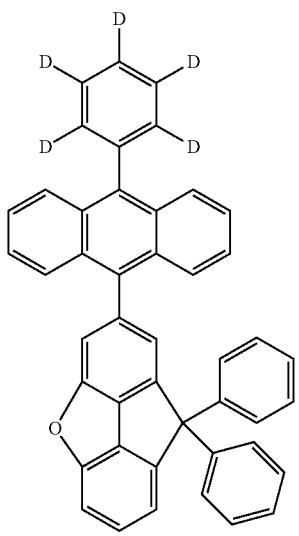

<Chemical Formula 2>

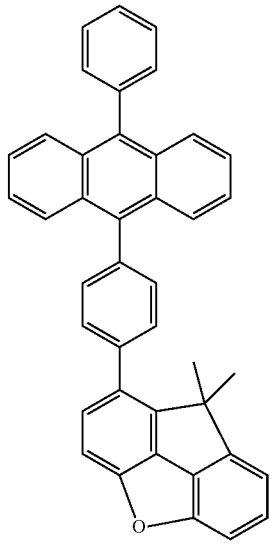

<Chemical Formula 3>
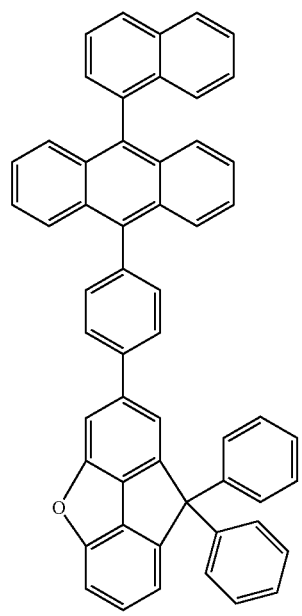
<Chemical Formula 4>
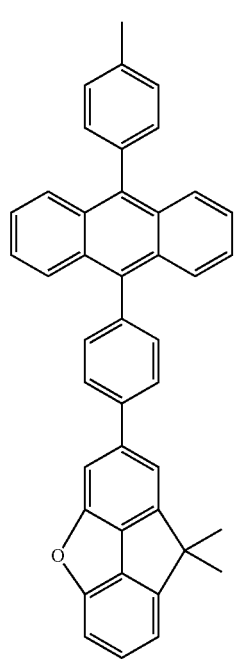
<Chemical Formula 5>
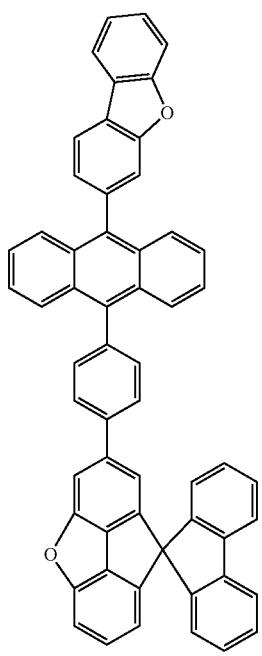
<Chemical Formula 6>
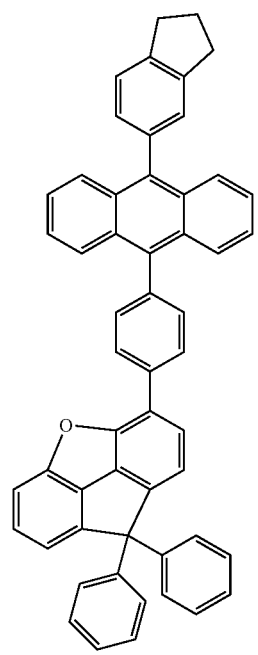

<Chemical Formula 7>
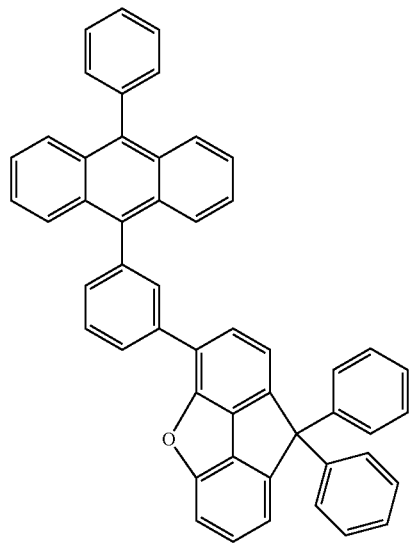
<Chemical Formula 8>
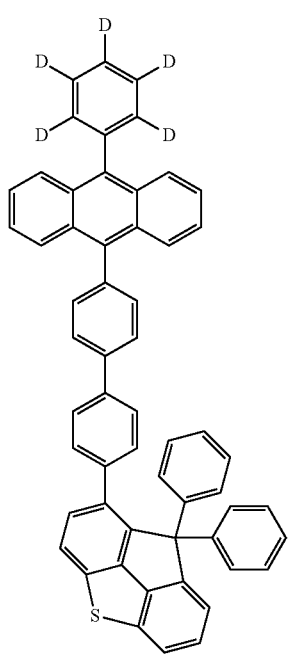
<Chemical Formula 9>
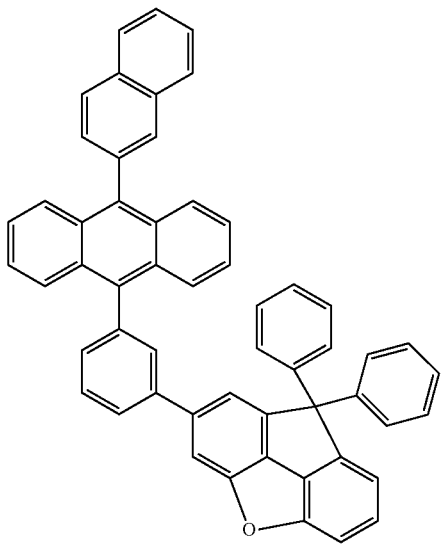
<Chemical Formula 10>
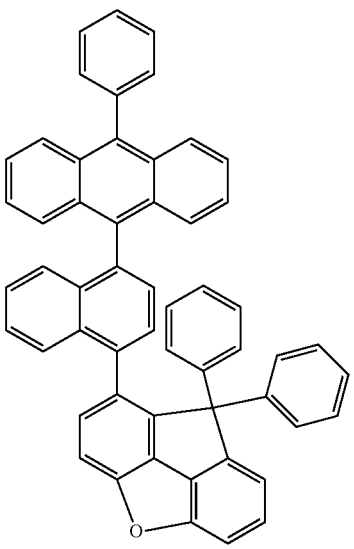

<Chemical Formula 11>
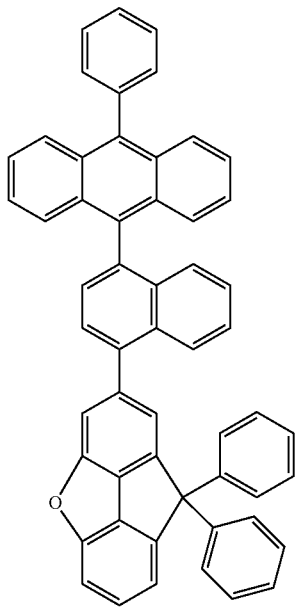
<Chemical Formula 12>
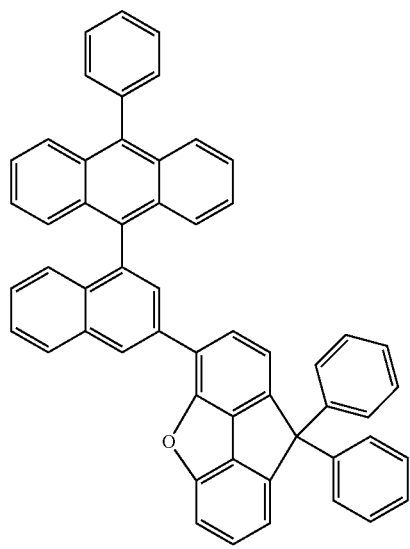
<Chemical Formula 13>
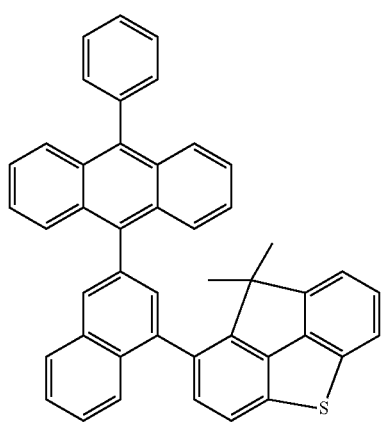
<Chemical Formula 14>
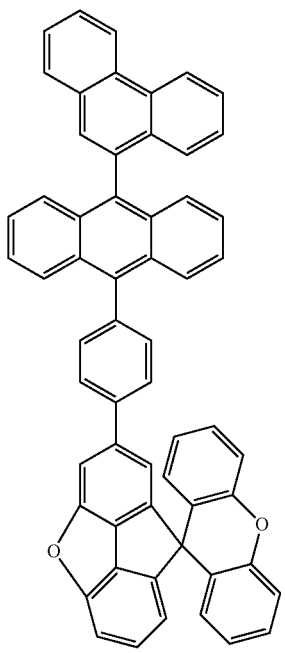
<Chemical Formula 15>
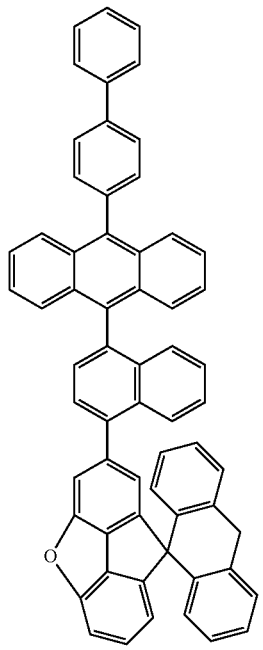

<Chemical Formula 16>
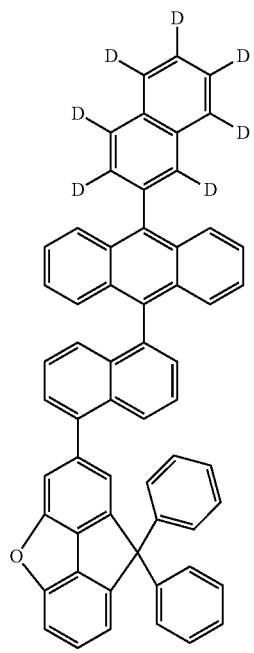
<Chemical Formula 17>
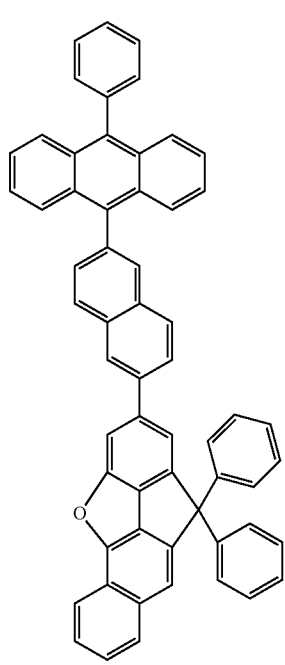
<Chemical Formula 18>
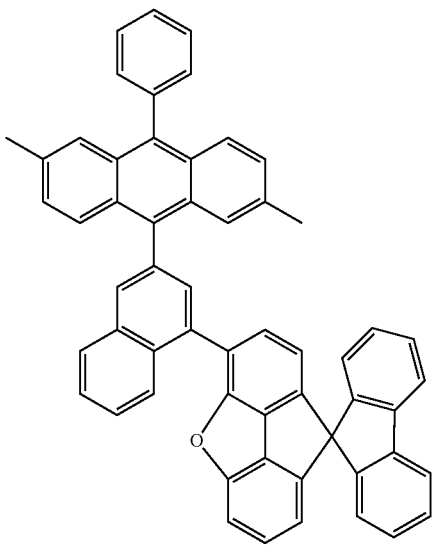
<Chemical Formula 19>
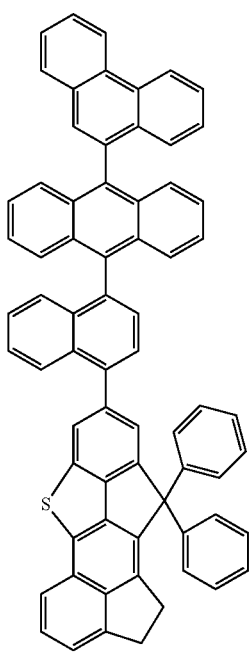

<Chemical Formula 20>
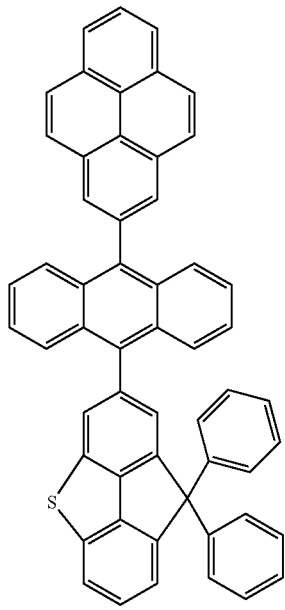
<Chemical Formula 21>
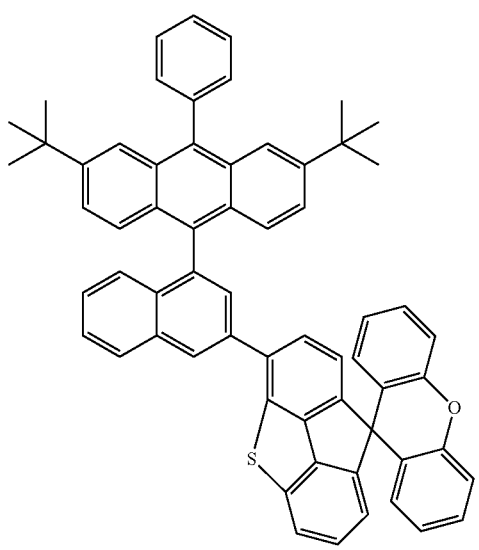
<Chemical Formula 22>
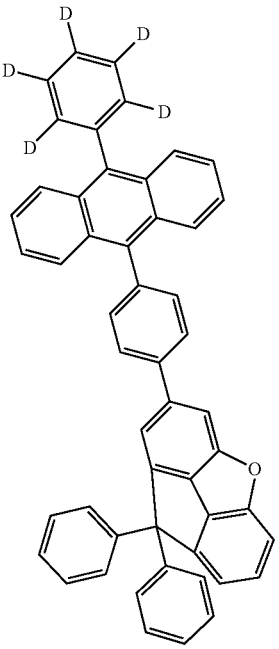
<Chemical Formula 23>
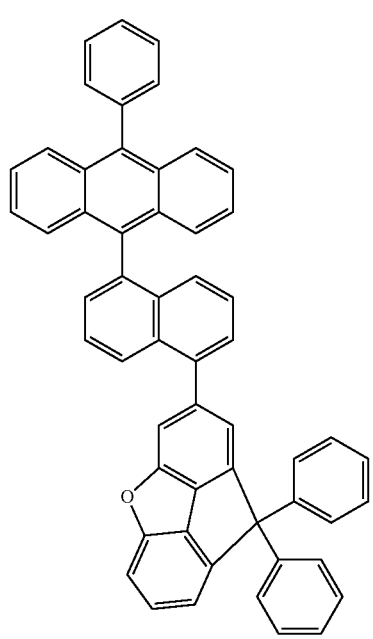

-continued

<Chemical Formula 24>

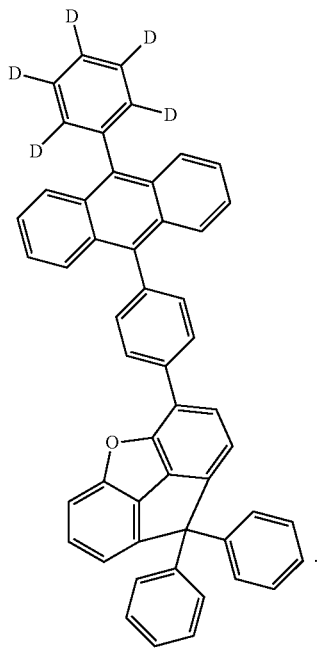

10. An organic light-emitting diode, comprising:
a first electrode;
a second electrode facing the first electrode; and
an organic layer interposed therebetween, wherein the organic layer contains the organic luminescent compound of any one of claim 1.

11. The organic light-emitting diode as set forth in claim 10, wherein the organic layer comprises at least one of a hole injecting layer, a hole transport layer, a functional layer capable of both hole injection and hole transport, a light-emitting layer, an electron transport layer, and an electron injecting layer.

12. The organic light-emitting diode as set forth in claim 11, wherein the organic layer interposed between the first electrode and the second electrode is a light-emitting layer composed of a host and a dopant, the organic luminescent compound serving as the host.

13. The organic light-emitting diode as set forth in claim 11, wherein at least one selected from among the layers is deposited using a single-molecule deposition process or a solution process.

14. The organic light-emitting diode as set forth in claim 10, wherein the organic luminescent compound as set forth in claim 1, wherein the organic light-emitting diode is used for a device selected from among a flat display device, a flexible display device, a monochrome or grayscale flat illumination device, and a monochrome or grayscale flexible illumination device.

* * * * *